US010709434B2

(12) United States Patent
Friedrich et al.

(10) Patent No.: US 10,709,434 B2
(45) Date of Patent: Jul. 14, 2020

(54) SURGICAL ACCESS SYSTEMS AND METHODS

(71) Applicant: GLOBUS MEDICAL. INC., Audubon, PA (US)

(72) Inventors: Adam Friedrich, Cinnaminson, NJ (US); Matthew Bechtel, Norristown, PA (US); Jason Cianfrani, Norristown, PA (US); Ryan Mammele, Conshohocken, PA (US)

(73) Assignee: Globus Medical, Inc., Audubon, PA (US)

( * ) Notice: Subject to any disclaimer, the term of this patent is extended or adjusted under 35 U.S.C. 154(b) by 207 days.

(21) Appl. No.: 13/937,960

(22) Filed: Jul. 9, 2013

(65) Prior Publication Data

US 2015/0018623 A1    Jan. 15, 2015

(51) Int. Cl.
*A61B 17/02* (2006.01)

(52) U.S. Cl.
CPC ...... *A61B 17/0206* (2013.01); *A61B 17/0293* (2013.01)

(58) Field of Classification Search
CPC ....... A61B 1/32; A61B 17/02; A61B 17/0206; A61B 17/0293; A61B 2017/0256
USPC .......................... 600/204, 219, 224, 226–234
See application file for complete search history.

(56) References Cited

U.S. PATENT DOCUMENTS

| | | | | |
|---|---|---|---|---|
| 5,755,660 A * | 5/1998 | Tyagi | ................ | A61B 17/0206 600/205 |
| 5,902,233 A * | 5/1999 | Farley | ................ | A61B 17/0206 600/213 |
| 5,928,139 A * | 7/1999 | Koros | ................ | A61B 17/0206 600/205 |
| 5,944,658 A * | 8/1999 | Koros | ................ | A61B 17/0206 600/231 |
| 5,954,635 A | 9/1999 | Foley | | |
| 6,206,822 B1 | 3/2001 | Foley | | |
| 6,468,205 B1 | 10/2002 | Mollenauer | | |
| 6,554,768 B1 * | 4/2003 | Leonard | ......................... | 600/213 |
| 6,921,364 B2 | 7/2005 | Mollenauer | | |
| 8,257,255 B2 * | 9/2012 | Farley | .................... | A61B 17/02 600/201 |
| 2006/0069315 A1 * | 3/2006 | Miles et al. | ................... | 600/219 |
| 2007/0093696 A1 * | 4/2007 | Sharratt | ................ | A61B 17/02 600/235 |
| 2007/0100212 A1 * | 5/2007 | Pimenta et al. | .............. | 600/210 |
| 2009/0105547 A1 * | 4/2009 | Vayser et al. | .................. | 600/228 |
| 2009/0204148 A1 * | 8/2009 | Lenke | .................... | A61B 17/02 606/246 |
| 2010/0210917 A1 | 8/2010 | Fallin | | |
| 2010/0217089 A1 * | 8/2010 | Farley | .................... | A61B 17/02 600/213 |
| 2010/0222644 A1 * | 9/2010 | Sebastian et al. | ............ | 600/228 |

(Continued)

*Primary Examiner* — Amy R Sipp

(57) ABSTRACT

A method for retracting tissue in a surgical procedure includes inserting a first blade of a retractor system into an incision in a body of a patient. The retractor system includes a first articulating arm and a second articulating arm. The first articulating arm is coupled to a retractor assembly blade. The retractor assembly blade has a handle portion and the first blade. The second articulating arm is coupled to a bracket securing a second blade. The method includes retracting tissue using the first blade, inserting the second blade into the incision in the body of the patient and retracting tissue using the second blade.

20 Claims, 37 Drawing Sheets

(56) References Cited

U.S. PATENT DOCUMENTS

| | | | |
|---|---|---|---|
| 2010/0256454 A1* | 10/2010 | Farley | A61B 17/02 600/210 |
| 2011/0087074 A1* | 4/2011 | Hardenbrook | A61B 17/0206 600/210 |
| 2012/0010472 A1* | 1/2012 | Spann | A61B 17/02 600/214 |
| 2012/0245431 A1* | 9/2012 | Baudouin et al. | 600/213 |
| 2012/0296171 A1* | 11/2012 | Lovell | A61B 17/0206 600/213 |
| 2013/0103103 A1 | 4/2013 | Mire | |
| 2013/0204091 A1* | 8/2013 | Menendez | A61B 17/02 600/228 |
| 2013/0225932 A1* | 8/2013 | Smith | A61B 1/313 600/206 |

* cited by examiner

SURGICAL ACCESS SYSTEMS AND METHODS

TECHNICAL FIELD

This description relates to surgical access systems and methods. More specifically, the description relates to a surgical access system and method to access the spine of a patient.

BACKGROUND

Retractor systems may be used in a variety of different surgical procedures to provide an opening through which the doctor may access the surgical site. In spinal surgeries, for example, a retractor system may be used to provide the surgeon with access to the patient's spine. The opening created by the retractor system may, for example, enable the doctor to insert surgical instruments into the body or enable visualization of the surgical site using x-ray.

Traditional spine procedures may involve bluntly dissecting through tissue and muscles to treat the appropriate levels of the spine. Thus, there is a need that allows for a more refined and controlled approach to spine procedures.

SUMMARY

According to one general aspect, a method for retracting tissue in a surgical procedure includes inserting a first blade of a retractor system into an incision in a body of a patient. The retractor system includes a first articulating arm and a second articulating arm. The first articulating arm is coupled to a retractor assembly blade. The retractor assembly blade has a handle portion and the first blade. The second articulating arm is coupled to a bracket securing a second blade. The method includes retracting tissue using the first blade, inserting the second blade into the incision in the body of the patient and retracting tissue using the second blade.

Implementations may include one or more of the following features. For example, the method of may further include independently positioning the first blade and the second blade using the first articulating arm and the second articulating arm, respectively. Retracting tissue using the first blade may include retracting the peritoneum anteriorly out of a surgical corridor. Retracting tissue using the second blade may include retracting a posterior wall of the surgical corridor.

The retractor assembly blade may include a hinge mechanism connecting the handle portion and the first blade and the method may include positioning the first blade at an angle relative to the handle portion using the hinge mechanism.

The method may further include prior to inserting the first blade of the retractor system into the incision, inserting a flexible retractor into the incision to provide a surgical corridor to a surgical sit The method may further include inserting a second retractor system into the incision. The second retractor system may include a frame having a plurality of blades and a plurality of movable arms with each of the blades coupled to the frame through one of the movable arms. The method may include angulating each of the blades of the second retractor system. The method may further include retracting each of the blades of the second retractor system. Inserting the second retractor system may include inserting the second retractor system into the incision in a closed position. The plurality of blades may include a single posterior blade and two cephalad-caudal blades. The method may further include inserting at least one light cable through at least one of the blades to illuminate a surgical site.

In another general aspect, a medical device includes a first mounting bracket, a first articulating arm coupled to the first mounting bracket, a second articulating arm coupled to the first mounting bracket, and a retractor assembly blade coupled to the first articulating arm. The retractor assembly blade has a handle portion and a first blade. A second mounting bracket is coupled to the second articulating arm. The second mounting bracket secures a second blade.

Implementations may include one or more of the following features. For example, the first blade and the second blade may be independently positioned using the first articulating arm and the second articulating arm, respectively. The retractor assembly blade may include a hinge mechanism connecting the handle portion and the first blade. The hinge mechanism enables the first blade to move and lock in multiple different positions relative to the handle portion. The handle portion of the retractor assembly blade may include an elongate member with a first mounting location on one side of the elongate member and a second mounting location on an opposite side of the elongate member, with either of the first mounting location or the second mounting location used to couple to the first articulating arm. The second mounting bracket may include a first mounting location on one side of the second mounting bracket and a second mounting location on an opposite side of the second mounting bracket, with either of the first mounting location or the second mounting location used to coupled to the second articulating arm.

In other example embodiments, the second mounting bracket may include a first mounting location on one side of the second mounting bracket and a second mounting location on an opposite side of the second mounting bracket to enable the second mounting bracket to couple to two articulating arms.

In another general aspect, a method for retracting tissue in a surgical procedure includes inserting a flexible retractor into an incision in a body of a patient to provide a surgical corridor to a surgical site and inserting a first blade of a retractor system into the incision in the body of the patient through the flexible retractor. The retractor system includes a first articulating arm and a second articulating arm. The first articulating arm is coupled to a retractor assembly blade. The retractor assembly blade has a handle portion and the first blade. The second articulating arm is coupled to a bracket securing a second blade. The method includes retracting tissue using the first blade, inserting the second blade into the incision in the body of the patient, and retracting tissue using the second blade. Sequential dilation is performed using a plurality of dilators. The method includes inserting a second retractor system into the incision over a largest of the dilators. The second retractor system includes a frame having a plurality of blades and a plurality of movable arms with each of the blades coupled to the frame through one of the movable arms. The method includes angulating each of the blades of the second retractor system and retracting each of the blades of the second retractor system.

Implementations may include one or more of the following features. For example, the method may further include independently positioning the first blade and the second blade using the first articulating arm and the second articulating arm, respectively.

The details of one or more implementations are set forth in the accompanying drawings and the description below.

Other features will be apparent from the description and drawings, and from the claims.

DETAILED DESCRIPTION

Detailed implementations of the present invention are disclosed herein; however, it is to be understood that the disclosed implementations are merely examples of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting, but rather to provide an understandable description of the invention.

The terms "a" or "an," as used herein, are defined as one or more than one. The term "another," as used herein, is defined as at least a second or more. The terms "including" and/or "having", as used herein, are defined as comprising (i.e., open transition).

The devices and methods (or techniques) described herein are generally directed to medical devices that can be used to provide direct visualization and access to a surgical site within a body of a patient. More specifically, the system and techniques described provides surgical instrumentation and method of use which allows for direct visualization of the muscle layers and corresponding nerves to avoid complications during and after a spinal fusion procedure, such as a lateral lumbar fusion surgery.

The term patient may be used hereafter for a person who benefits from the medical device or the methods disclosed in the present invention. For example, the patient may be a person whose body receives the medical device disclosed by the present invention in a surgical treatment. For example, in some embodiments, the patient may be a human female, human male, or any other mammal.

Figure 1:
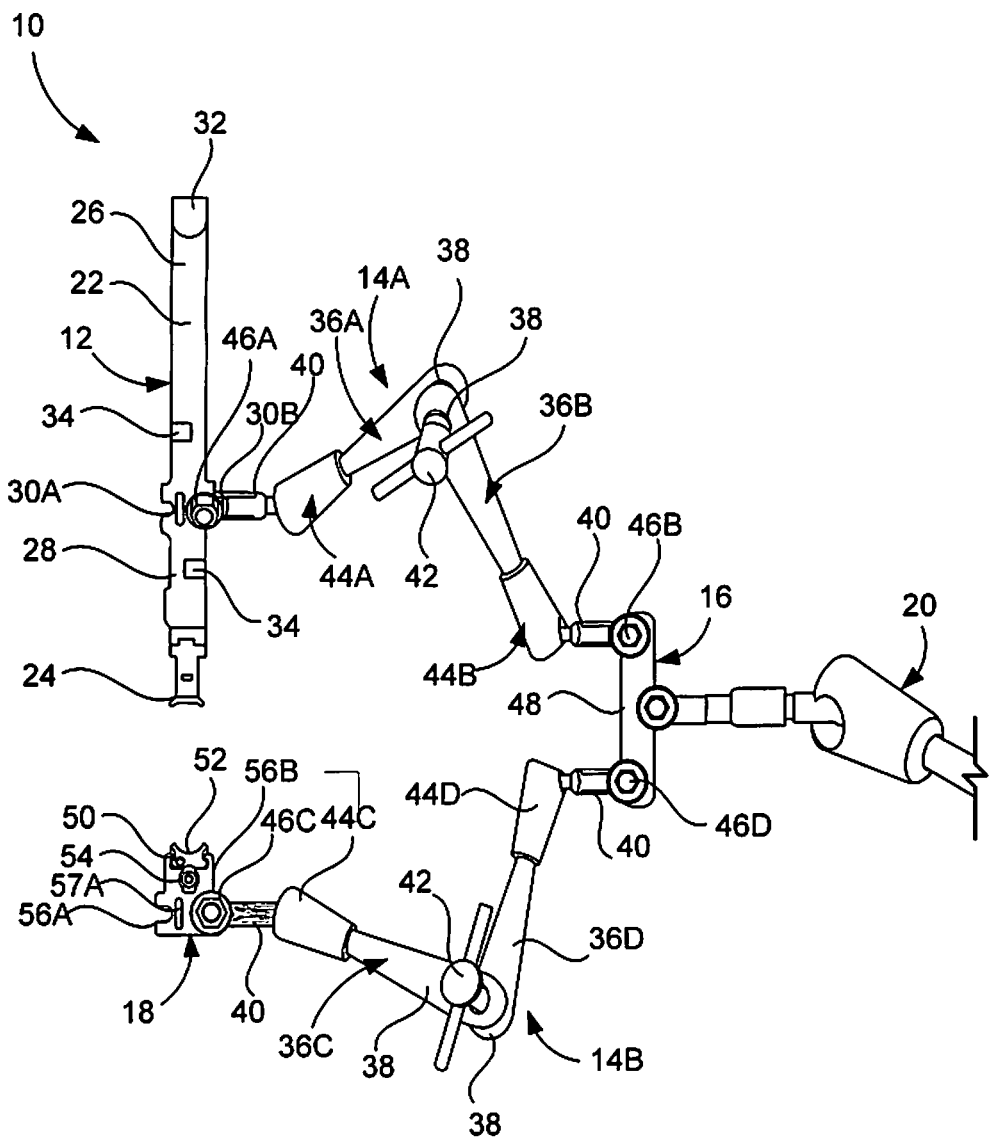
FIG. 1 is a perspective view of a medical device according to an embodiment of the invention.

FIG. 1 is a perspective view of a medical device 10 according to an embodiment of the invention. The medical device 10 may be one of the components of the surgical system to allow for direct visualization and access during spinal surgery. In one example embodiment, medical device 10 is a peritoneal retractor that may be used to retract tissue in a surgical procedure, as further described below with the use of the device and its use in a particular surgical technique. In other example embodiments, the medical device 10 may be used in other types of surgeries and surgical procedures.

The medical device 10 includes a retractor assembly blade 12, arms 14A and 14B, arm mounting bracket 16 (also referred to as mounting bracket 16) and blade mounting bracket 18 (also referred to as mounting bracket 18). The medical device 10 may be secured to a surgical table or other device using a mount 20. For example, the mount 20 may be a table mount that secures the medical device 10 to a bedrail or other rail or component on a surgical table.

The medical device 10 allows for multiple independent blades to be inserted into a patient and to provide direct access and visualization to the muscles and tissues near the spine. For example, the medical device 10 may include one blade as part of the retractor assembly blade 12 and a another blade that is connected to the blade mounting bracket 18. Both blades may be inserted into the surgical site to access and retract tissue.

The retractor assembly blade 12 may be secured and connected to the arm 14A. The retractor assembly blade 12 includes a handle portion 22 (or handle 22) and a blade portion 24. Examples of the retractor assembly blade 12 are illustrated in FIGS. 2-5 and described with respect to those figures in more detail below. The handle portion 22 may provide a grip area to allow a surgeon to hold and retract tissue by gripping the handle portion 22. The handle portion 22 includes a distal end 26 and a proximal end 28. The handle portion 22 at the proximal end 28 includes one or more connection points 30A and 30B for connecting to the arm 14A. The connection points 30A and 30B also may be referred to as mounting locations or arm mounting locations. The connection points 30A and 30B may be on either side of the handle portion 22. In this manner, the handle portion 22 may connect to the arm 14A on either side of the handle 22. In other example embodiments, the handle portion 22 may connect to two arms with one arm connected to connection point 30A and the other arm connected to connection point 30B.

The distal end 26 may include a curved portion 32. The curved portion 32 may allow a surgeon to grab or hold the curved portion and pull the retractor assembly blade 12 in a desired direction and/or orientation. The curved portion 32 may allow a doctor to position the retractor assembly blade 12 in a desired manner.

The blade portion 24 is connected to the handle portion 22 near the proximal end 28 of the handle portion 22. The blade 24 may be a removable component of the retractor assembly blade 12. Different types of blades may be used with the same handle portion 22. The blade 24 that may connect to the handle portion 22 may have varying lengths and/or widths, as illustrated in more detail in FIGS. 2-5.

The blade portion 24 may include a cannulation through at least a portion of its length from the proximal end to the distal end to allow for a self-retained light source. The self-retained light source (not shown) may be inserted through the blade cannulation and used to illuminate a surgical corridor and/or surgical site. The handle portion 22 may include one or more tabs 34 to hold a cable or other wire for the light source and to keep the cable out of the operative field.

The arms 14A and 14B allow maneuverability of the retractor assembly blade 12 and the mounting bracket blade 18 in the operative field in multiple directions and/or planes. While the description of one arm 14A may be described, it is understood that the description applies equally to the arm 14B. The arms 14A and 14B may be referred to as mini-articulating arms. Each arm 14A and 14B may be positioned independent of each other thus providing independent positioning and maneuverability of respective blades or blade assemblies attached to the articulating arms 14A and 14B.

Each arm 14A and 14B may include one or more smaller component arms 36A-36D. The smaller component arms 36A-36D each have a proximal end 38 and a distal end 40. The proximal end 38 on each of the arms 36A-36D may connect to or may provide a connection point to another arm. For example, the proximal end 38 on arm 36A provides a connection point to the proximal end 38 on arm component 36B. The smaller component arms 36A-36D may be joined to the other component arms in a number of ways including a rotationally captured fit, a pin and hole connection, a telescoping connection, a translation connection or similar connection. In this example embodiment, the proximal end of each smaller component arm includes a hole through which a pin 42 may be inserted to connect one arm to another arm. The pin 42 may be tightened and un-tightened to secure the arms in relation to one another.

Each of the arms 36A-36D may include a knob portion 44A-44D (or knob 44A-44D). In one example embodiment, the knob portions 44A-44D may be located between the proximal end and the distal end. The knob portions 44A-44D may be used to lock the arms in a desired position, The knobs may rotate from one position to at least one other position to lock and unlock the movement of the arms. For example, when the knob portion 44A-44D is in a first position the arm may be in a locked position. When the arm is locked in place, it may be prevented from further articulation and movement. When the knob is in a second position, the arm may be unlocked and capable of articulating into a desired position.

The distal end 40 of each of the arms 36A-36D includes a locking mechanism 46A-46D. The locking mechanisms 46A-46D provide a connection point to another component of the medical device 10. For example, the locking mechanism 46A-46D may connect and lock to a bracket, such as mounting bracket 16 or mounting bracket 16. In the illustrated example, component arm 36A includes a locking mechanism 46A that locks and connects to the retractor assembly blade 12. The component arm 36B includes a locking mechanism 46B that connects and locks to the mounting bracket 16. Similarly, component arm 36D includes a locking mechanism 46D that also connects to the mounting bracket 16. The component arms 36C includes a locking mechanism 46C that connects to the mounting bracket 18.

The locking mechanisms 46A-46D may include different types of locking features that provide a positive locking feature to connect the arms 14A and 14B to the brackets. Examples of locking mechanisms include, but are not limited to, tongue and groove, bolts and slot, screw and threaded hole, and interference fit. In the illustrated embodiment, a screw and threaded hole feature is used to connect the arms 14A and 14B to the brackets and/or retractor assembly blade.

While the illustrated embodiment shows to smaller component arms joined to make single articulating arms, it is possible that combinations of more than two smaller component arms may be used to form a single articulating arm. For example, component arm 36A and 36B form articulating arm 14A. In the same manner, component arm 36C and 36D form the articulating arm 14B.

In the illustrated embodiment, mounting bracket 16 includes three connection points (or mounting locations). In other example embodiments, the mounting bracket 16 may include more or less connection points. In this example, the bracket 16 may be referred to as a "Y-type" connector that includes a single attachment point on one side and multiple attachment points on the other side. The mounting bracket 16 may include an elongate member 48. In the illustrated embodiment, there are two connection points on one side of the elongate member 48 and one connection point on the other side of the elongate member 48. Arm 14A connects to the one connection point using the locking mechanism 46B to make a secure attachment to the bracket 16. Arm 14B makes a connection to the other connection point using the locking mechanism 46D to make a secure attachment to the bracket 16. The other connection point connects to the table arm 20 and provides a secure attachment to the table arm 20.

The mounting bracket 18 includes a slot 50 to accept a blade 52. The slot 50 may receive the blade 52 and lock the blade 52 into the slot 50 using the locking mechanism 54. In the illustrated embodiment, the locking mechanism 54 may also be referred to as a blade locking nut. The locking mechanism 50 may be rotated to a first position to allow the insertion and removal of the blade 52 into the mounting bracket 18. The locking mechanism 54 may be rotated or moved into a second position to lock the blade 52 into the bracket 18. When the locking mechanism 54 is in the second position, the blade 52 is prevented from being removed from the bracket 18.

The mounting bracket 18 includes multiple attachment points 56A and 56B. The attachment points may be on either side of the bracket 18. In this manner, the arm 14B may be connected to either side of the mounting bracket 18. In the illustrated embodiment, the attachment points 56A and 56B each include a slot (57A for connection point 56A) to receive the locking mechanism, such as locking mechanism 46C.

In use, the medical device 10 may be used to help retract the peritoneum out of the surgical corridor. The medical device 10 may be a peritoneal retractor that is inserted into an incision and used to retract the peritoneum out of the surgical corridor. The use of the medical device 10 is illustrated and described in more detail below with respect to the described surgical technique of FIGS. 12-38.

Figure 2:
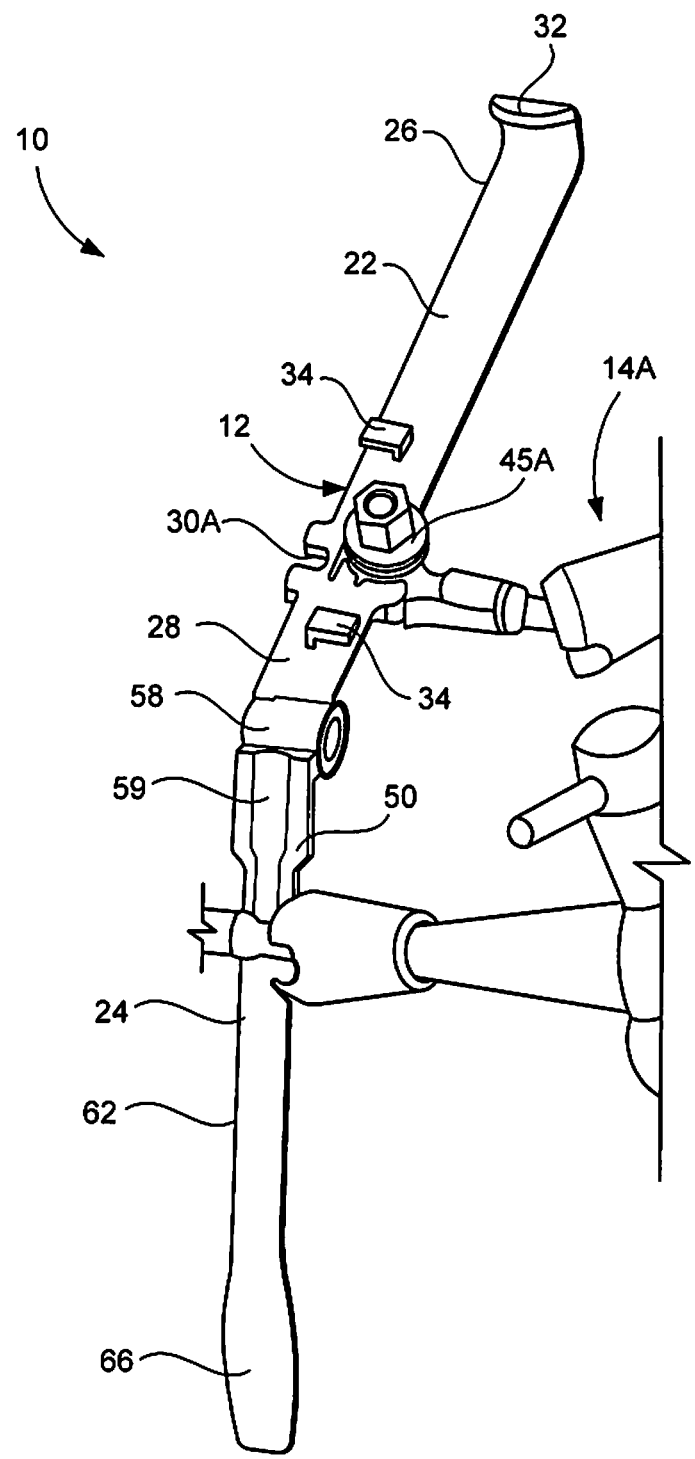
FIG. 2 is a perspective view of a retractor assembly blade of the medical device of FIG. 1 according to an embodiment of the invention.
Figure 3:
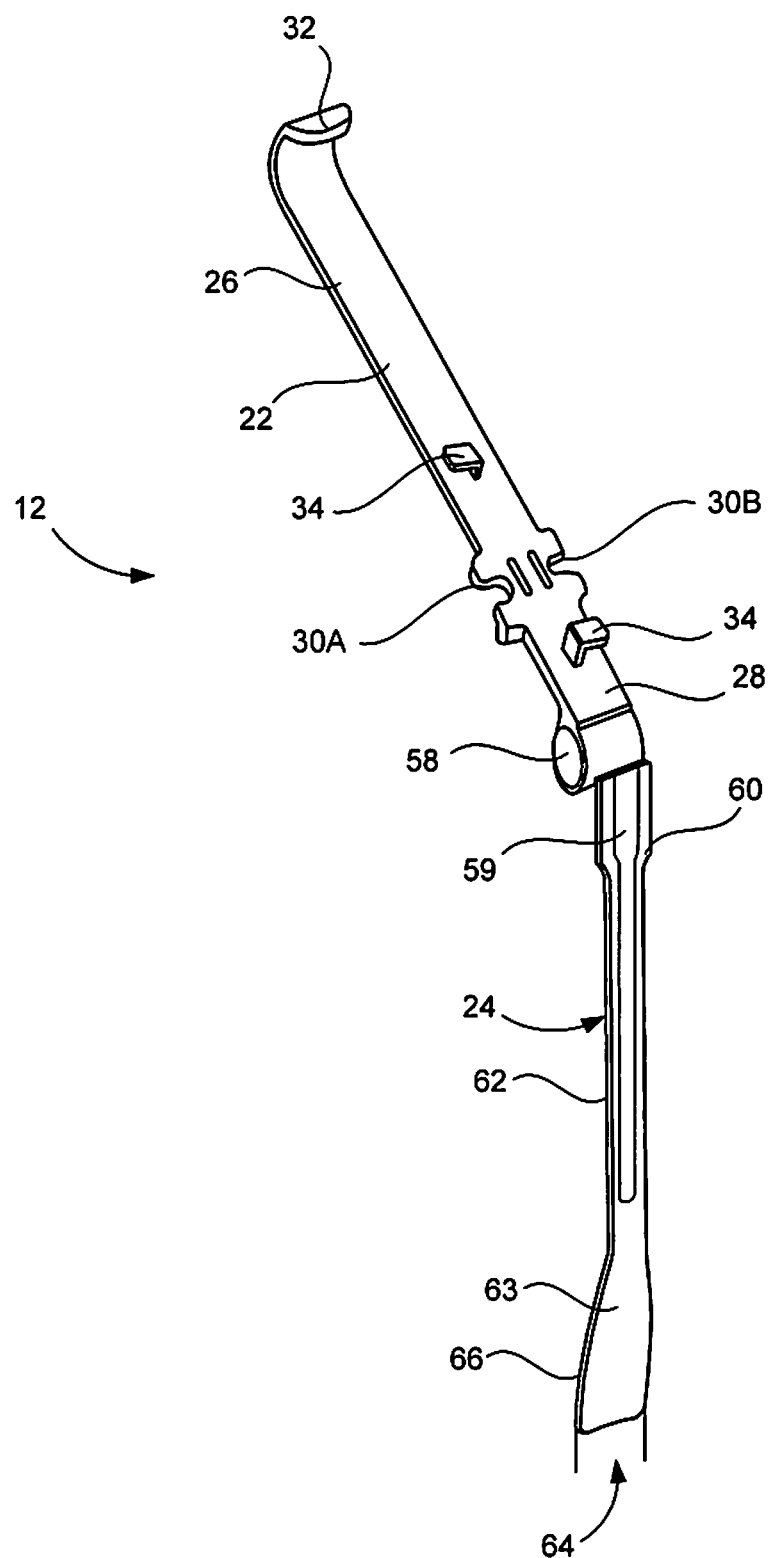
FIG. 3 is a perspective view of a retractor assembly blade of the medical device of FIG. 1 according to an embodiment of the invention.
Figure 4:
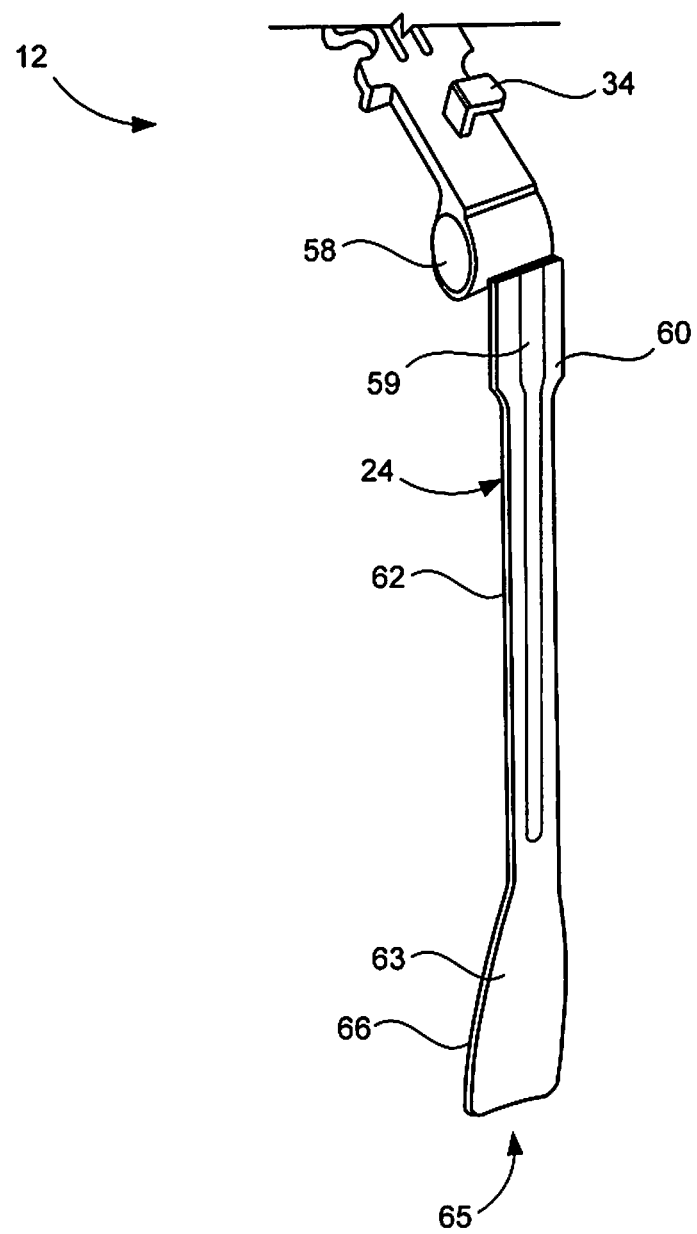
FIG. 4 is a partial perspective view of a retractor assembly blade of the medical device of FIG. 1 according to an embodiment of the invention.
Figure 5:
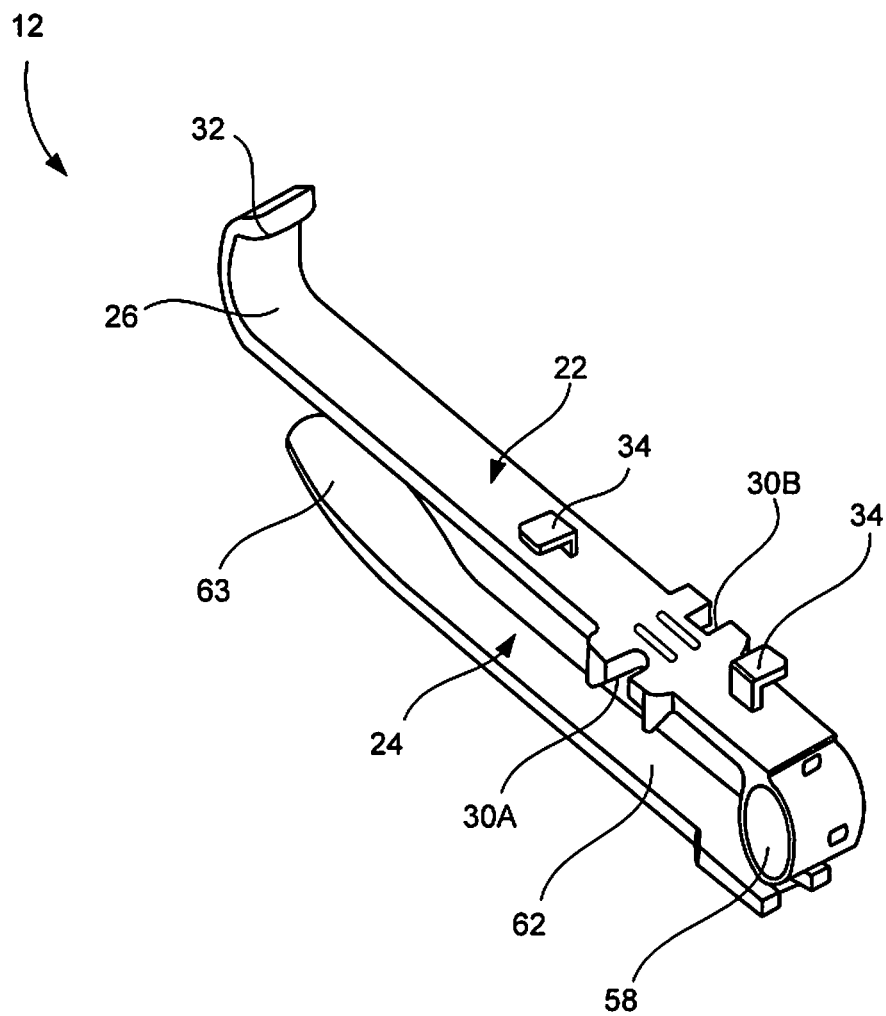
FIG. 5 is a perspective view of a retractor assembly blade in a folded position of the medical device of FIG. 1 according to an embodiment of the invention.

FIGS. 2-5 illustrate a portion of the medical device 10. In the illustrated example of FIG. 2, the portion of the medical device 10 illustrated includes the retractor assembly blade 12 connected to one of the articulating arms 14A. FIG. 3 illustrates the retractor assembly blade 12 in an open position, where the handle portion 22 and the blade portion 24 are open at an angle with respect to one another. The handle portion 22 and the blade portion 24 may rotate about a hinge mechanism 58. The hinge mechanism 58 may allow the handle portion 22 and the blade portion 24 to rotate about a point with respect to each other from a folded (or closed) position, as illustrated in FIG. 5, to an open position, as illustrated in FIGS. 2-4. The hinge mechanism 58 may be a push button type mechanism that when pushed allows the handle portion 22 and the blade portion 24 to be positioned through varying angles with respect to each other and when released may lock the portions into a desired position. For example, the handle portion 22 and the blade portion 24 may be rotated in multiple positions through 180°. The retractor assembly blade 12 may be locked into any one of the multiple positions along the movement of travel about the hinge mechanism 58. In other example embodiments, other types of hinge mechanisms may be used to enable the portions to rotate about each other and to lock into a desired position.

The blade portion 24 may be independent of the handle portion 22. In this manner, differing blade portions may be used with the same handle portion 22. The handle portion 22 may include a tongue 59 and the blade portion may include a slot 60 into which the blade and handle portion are slid in a tongue and groove fashion, which works to secure the blade portion into handle portion. The blade portion 24 may include a straight elongate member 62 and a curved portion 63 at a distal end of the elongate member 62 and the curved portion 63 may be of varying lengths and/or widths. The distal end 66 of the blade portion 24 may be blunted to prevent tissue damage. The curved portion 63 may be used to aid in the engagement of tissue material during a surgical procedure.

In the illustrated embodiment, the blade portion 24 may be concave on an inner surface and convex along an outer surface. The curved portion 63 may be spoon-shaped to allow for engagement of tissue at a surgical site. The elongate member 62 may be substantially linear. In other example embodiments, the elongate member 62 may include a slight curvature and be non-linear.

FIGS. 3 and 4 illustrate the retractor assembly blade 12 in full (FIG. 3) and in part (FIG. 4) without being attached to the rest of the medical device 10. In these illustrated embodiments of FIGS. 3 and 4, the blade portion 24 may have a varying width at the distal end 66. For example, in FIG. 3 the curved portion 63 has a first width 64. In FIG. 4, the distal end 66 at the curved portion 63 has a second width 65 that is different from the width 64 is illustrated in FIG. 3. In other example embodiments, different blades may have different lengths as well.

FIG. 5 illustrates the retractor assembly blade 12 in a folded (or closed) position. As discussed above, the handle portion 22 and the blade portion 24 may rotate about a hinge mechanism 58. In this example, the blade portion 24 has been rotated and disposed beneath the handle portion 22. The folded position also may be referred to as a closed position. The hinge mechanism 58 may include a push button to allow the unlocking of the portions with respect to each other and allow them to rotate from the folded or closed position to a different position through multiple different positions and angles with respect to each other.

Figure 6:
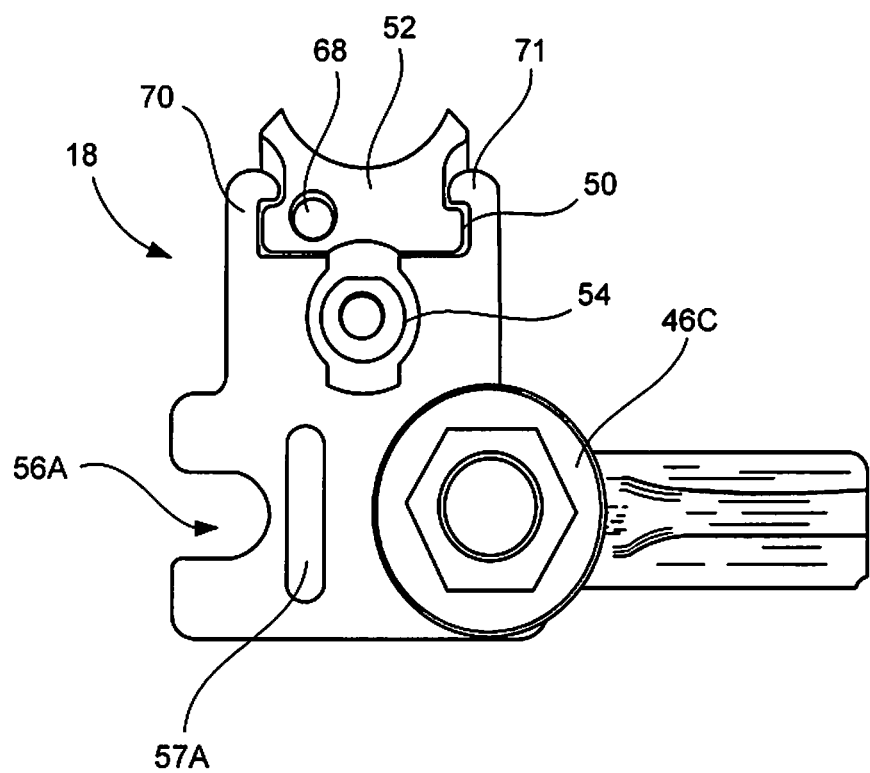
FIG. 6 is a top view of a mounting bracket of the medical device of FIG. 1 according to an embodiment of the invention.

FIG. 6 illustrates the mounting bracket 18. The mounting bracket 18, as described above, may be used to connect to one of the arms of the medical device 10 and to mount a blade 52 into the bracket 18. In this illustrated example, the mounting bracket 18 includes multiple connection points 56A and 56B (not shown in FIG. 6) to enable the bracket 18 to connect to one of the arms of the medical device 10. The bracket 18 is locked to the arm using the locking mechanism 46C on the arm.

In other example embodiments, the bracket 18 may be locked to the arm using the other connection 56A. In other example embodiments, two articulating arms may be connected to the bracket 18.

As discussed above with respect to FIG. 1, the locking mechanism 54 may be rotated between positions to allow the insertion and removal of the blade 52 into the bracket 18. In this example, FIG. 6 illustrates a top view of the bracket 18 and the blade 52. The blade 52 may include a cannulation 68. The cannulation 68 may be used to insert a light source through the blade to provide illumination at the distal end of the blade. The illumination provided by the light through the cannulation 68 helps to illuminate the surgical site.

The bracket 18 includes a hook 70 and a hook 71 to engage the blade 52 and hold the blade into the slot 50. In other example embodiments, other types of mechanisms may be used to hold the blade 52 into the slot 50.

In one example embodiment, multiple arms may be used to connect to the same bracket 18. For example, one arm may be connected to one side of the bracket and another arm may be connected to the other side of the bracket. Each of the arms may be locked into position to secure the bracket onto the arm.

Figure 7:
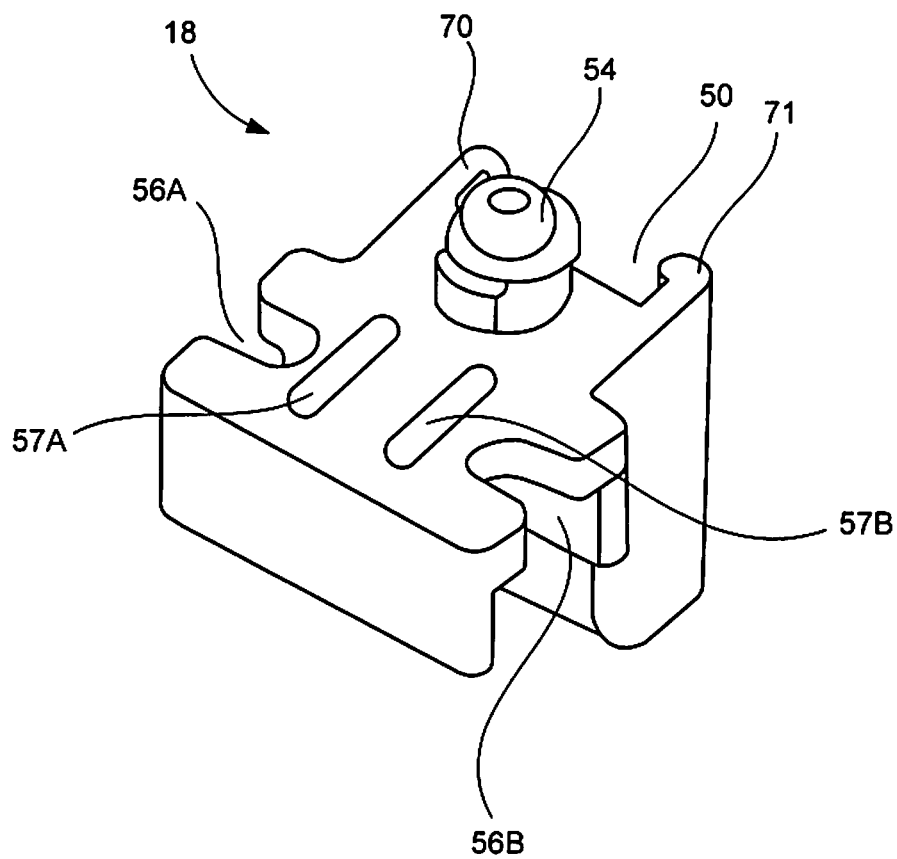
FIG. 7 is a perspective view of a mounting bracket of the medical device of FIG. 1 according to an embodiment of the invention.

FIG. 7 illustrates the mounting bracket 18 as a separate component. As discussed above, the mounting bracket 18 includes multiple connection points 56A and 56B. In this manner, multiple arms may be connected to either side of the bracket 18.

Figure 8:
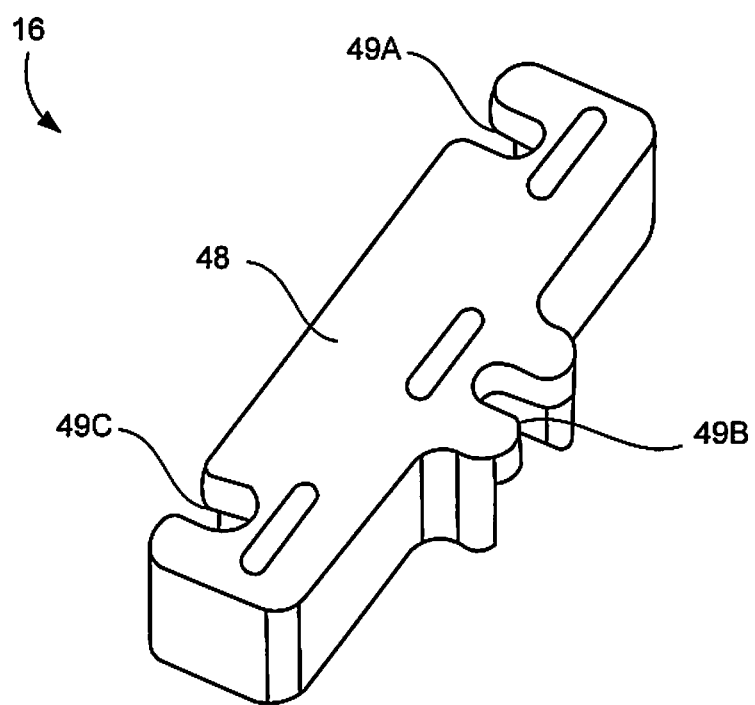
FIG. 8 is a perspective view of a mounting bracket of the medical device of FIG. 1 according to an embodiment of the invention.

FIG. 8 illustrates the mounting bracket 16. The mounting bracket 16 may be used as an adapter to attach the arms 14A and 14B to a larger table arm. In the illustrated example, the mounting bracket 16 includes three mounting locations to interface with the different arm connections. The mounting locations 49A-49C provide the connection points to the arms 14A, 14B and 20.

As discussed above, the mounting bracket 16 includes an elongate member 48. The elongate member 48 includes the connection points 49A-49C. While the illustrated example shows three connection points, other numbers of connection points may be included along the elongate member 48.

Figure 9:
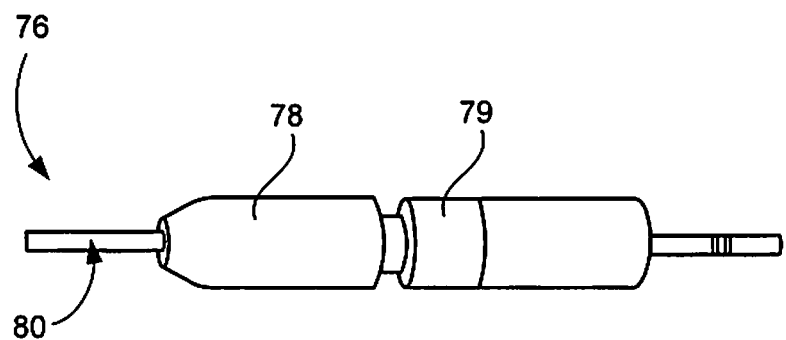
FIG. 9 is a perspective view of a k-wire stop according to an embodiment of the invention.
Figure 10:
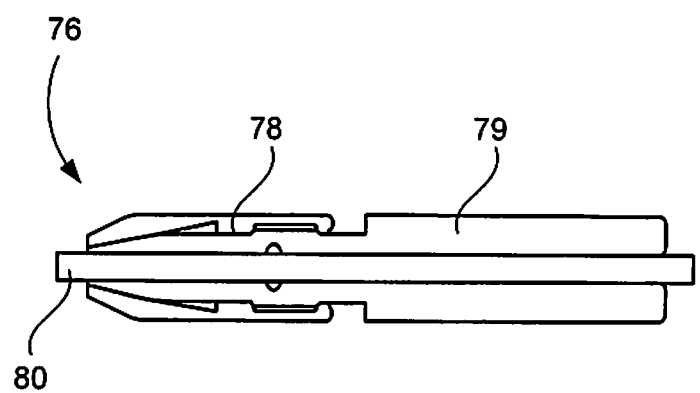
FIG. 10 is a cross-section view of the k-wire stop of FIG. 9 according to an embodiment of the invention.
Figure 11:
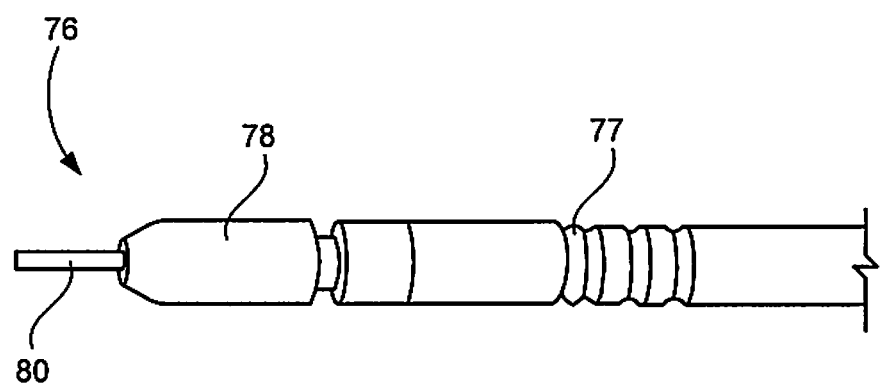
FIG. 11 is a perspective view of a k-wire stop according to an embodiment of the invention.

FIGS. 9-11 illustrate K-wire stop 76. FIG. 9 illustrates the K-wire stop 76, FIG. 10 illustrates a cross-section of the K-wire stop 76 and FIG. 11 illustrates the K-wire stop 76 resting on a dilator 77. The K-wire stop 76 includes a nut 78 and a body 79. The K-wire stop 76 grips a K-wire 80 and holds it in a desired location while inserted into an initial dilator 77. With the K-wire 80 inserted into the assembly, rotating the nut 78 will clamp the body 79 onto the K-wire. The use of the K-wire stop 76 is described in more detail below with respect to FIGS. 12-38 as used in the surgical technique as described below.

FIGS. 12-38 describe an example surgical technique using one or more of the components from medical device 10 in cooperation with one or more other components in the context of the surgical technique. In one exemplary embodiment, the technique includes accessing a desired surgical site, which may be, for example, a spinal disc in a lateral approach under direct visualization. The following exemplary technique describes a set of steps in a particular order; however, it should be understood that changing the order the steps or not completing all the steps is contemplated.

Figure 12:
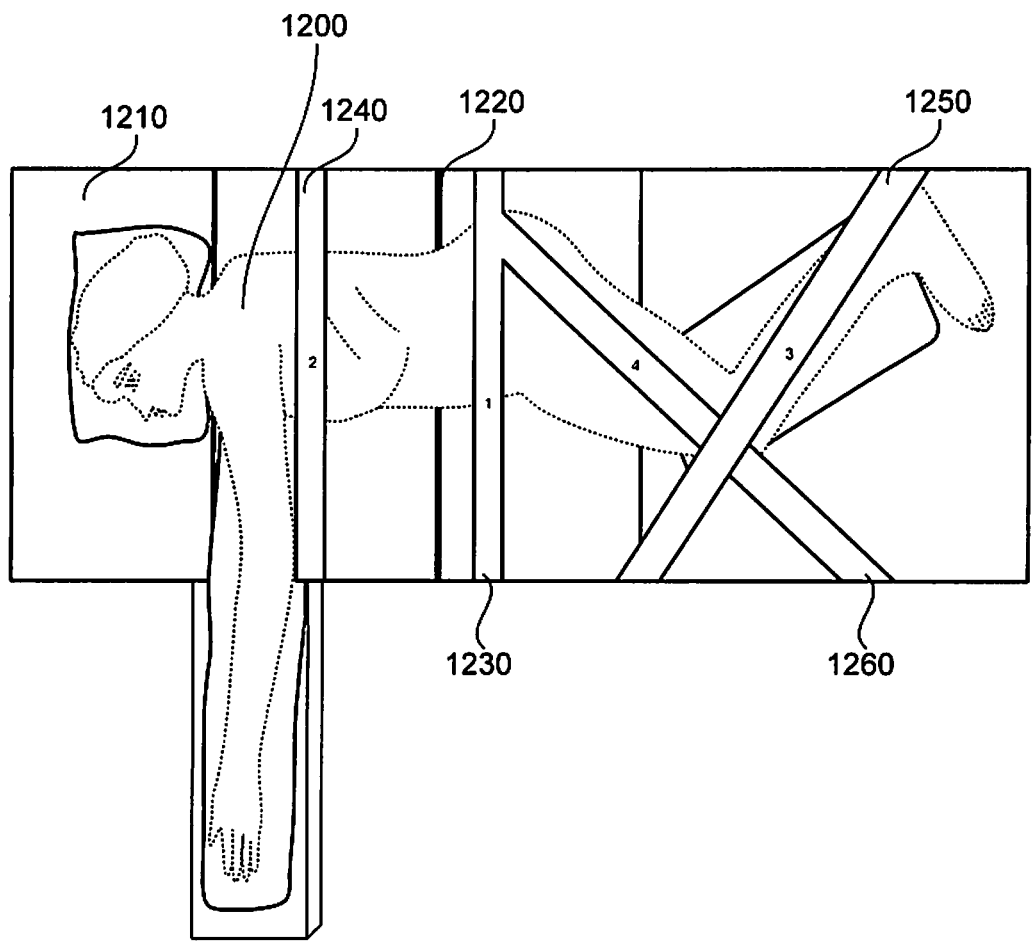
FIGS. 12-38 illustrate steps of a surgical technique and the medical devices used in the surgical technique according to an embodiment of the invention.
Figure 13:
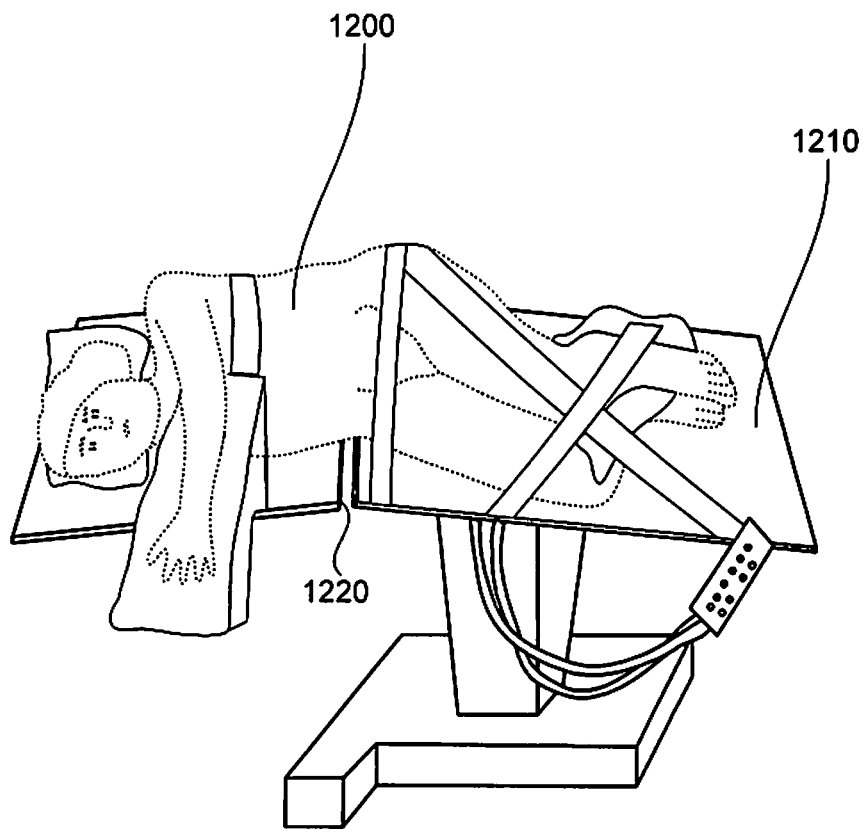

FIGS. 12 and 13 illustrate a first step of the surgical technique. The first step includes patient preparation and patient positioning. The patient 1200 is placed on a flexible surgical table 1210. The patient may be placed on the flexible surgical table 1210 in a true 90° right lateral decubitus position so that the iliac crest is just over a desired portion of a surgical table 1210 that the patient 1200 is placed upon. As illustrated in FIG. 13, the surgical table 1210 may be capable of bending or breaking in one or more places, such as location 1220. The desired position may be to place the patient 1200 over such a break 1220 as shown in FIG. 13. In an example embodiment, the table 1200 should be flexed to open the interval between the 12$^{th}$ rib and the iliac crest and provide direct access to the disk space.

As shown in FIG. 12 the patient may be secured to the table 1200 at the following locations (1) just beneath the iliac crest 1230; (2) over the thoracic region, just under the shoulder 1240; (3) from the back of the table, over the ankle 1250; and (4) past the knee to the front of the table 1250.

Figure 14:
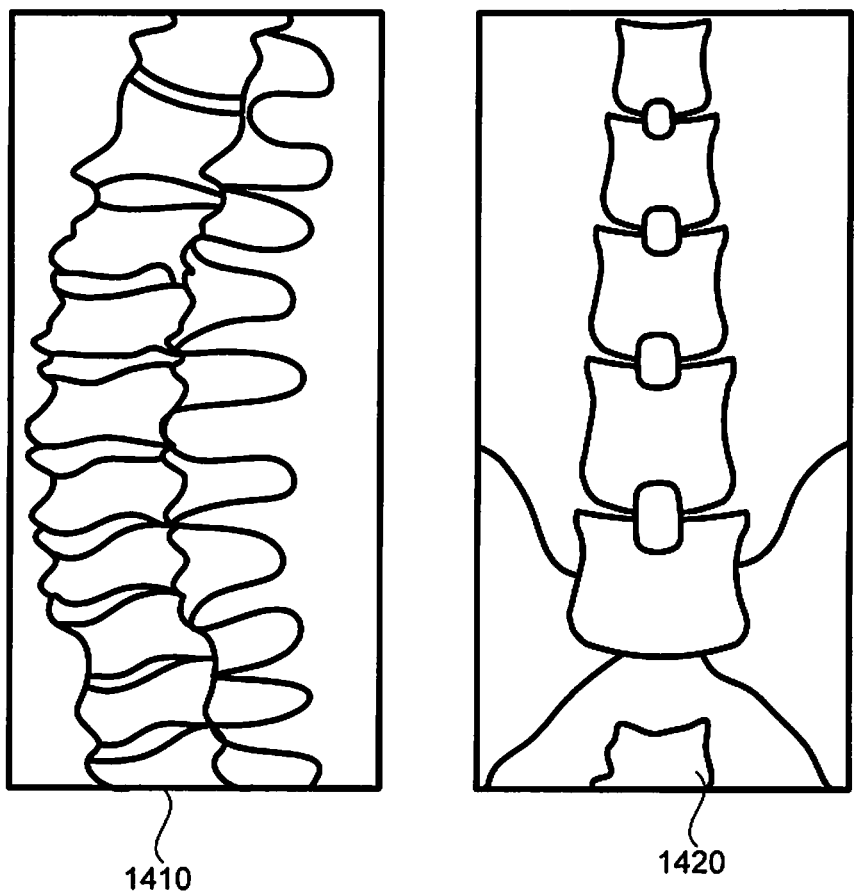

As part of the surgical technique of step one, fluoroscopy may be used to confirm accurate placement and positioning of the patient to allow the appropriate access to the desired surgical site. FIG. 14 illustrates two images 1410 and 1420. These example images illustrate a lateral image 1410 and an AP image 1420. The surgical table should be adjusted so that the C-arm provides true AP images when at 0° and true lateral images at 90°.

Figure 15:
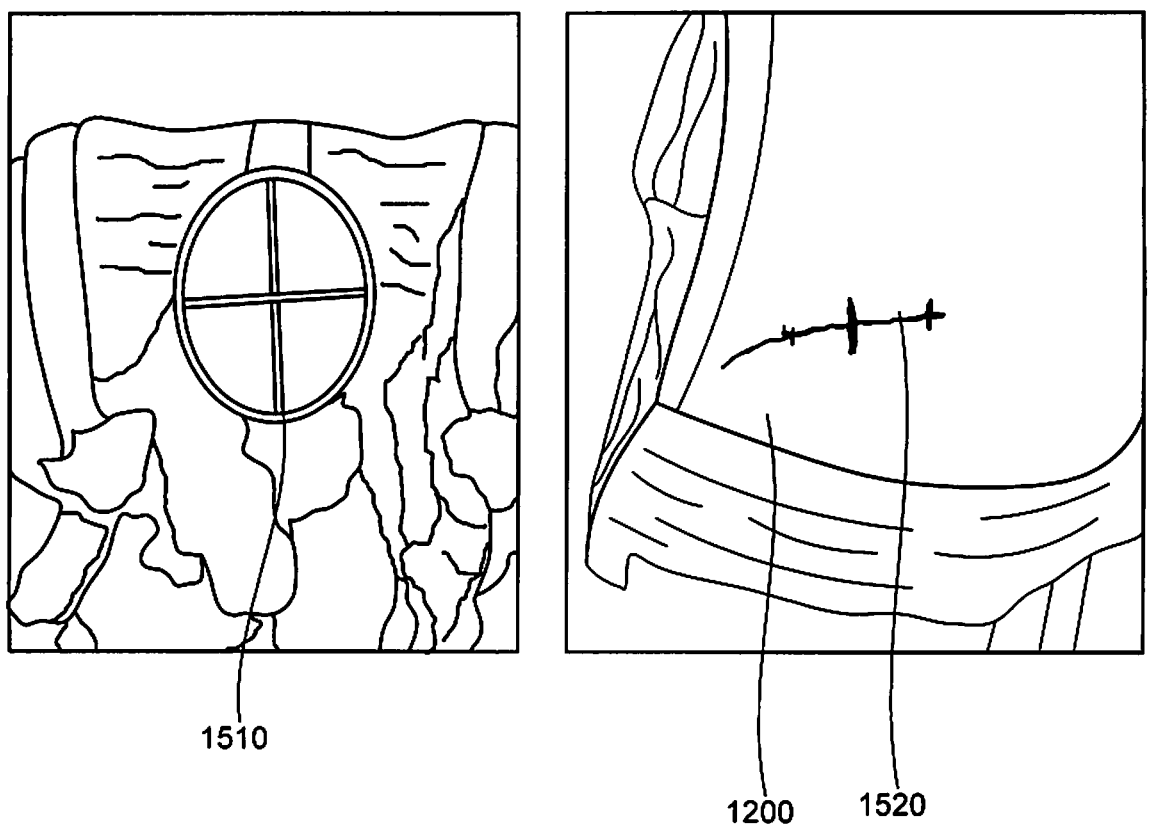

Also as part of step one of the surgical technique, FIG. 15 illustrates the use of an incision locator 1510 to identify the incision location on the patient. For example, the operative area is carefully cleaned and the incision locator 1510 may be used under fluoroscopy to identify the middle of the disk space to be fused. An access incision mark 1520 may be traced on the patient's skin to indicate the position and insertion site for the medical components to be used during the surgical technique. For example, the access incision mark 1520 may be used to indicate the position and insertion site for the medical device 10, as well as other components to be used during the procedure.

Figure 16:
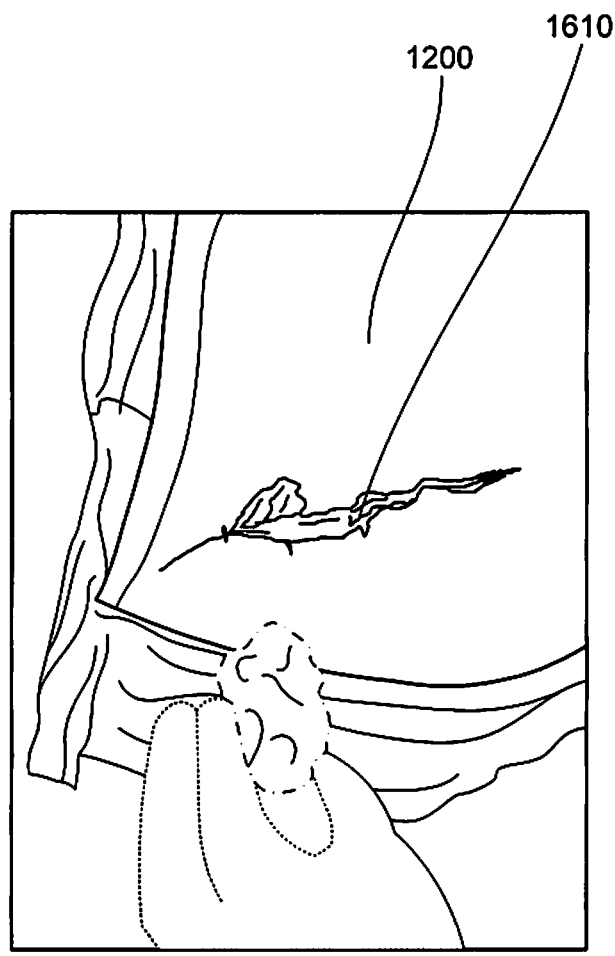
Figure 17:
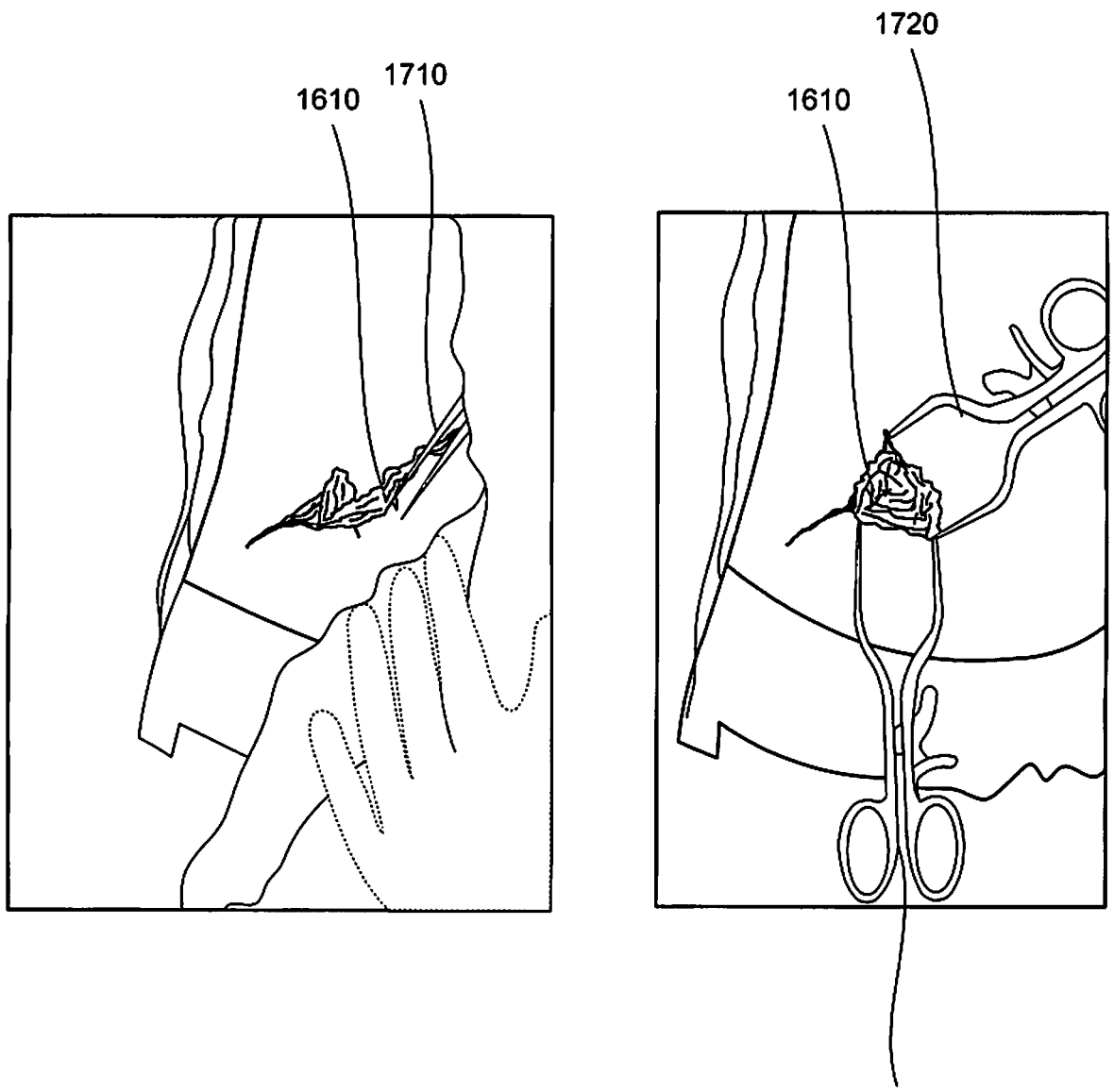

FIGS. 16 and 17 illustrate a next step in the surgical technique. In the exemplary technique, the next step includes making an incision in the patient about the desired surgical destination. For example, the next step may include making an incision 1610 above the spinal disc that is to be addressed. In one example embodiment, the incision 1610 may be sized such that allows for eventual direct visualization of the surgical site. The incision size may vary based on the amount of eventual visualization desired. One exemplary incision size may be 2 inches. For example, the incision 1610 may be a small, oblique 2 inch incision above the targeted disk space. In other example embodiments, multiple incisions may be used if there are going to be multiple desired surgical destinations.

Once the incision 1610 is made, in an example technique, dissection through the skin fascia and adipose tissue may be accomplished using bipolar forceps 1710, as illustrated in FIG. 17. The initially dissected tissue may be held in place via the use of a retractor, such as Wietlaner Retractor 1720.

Figure 18:
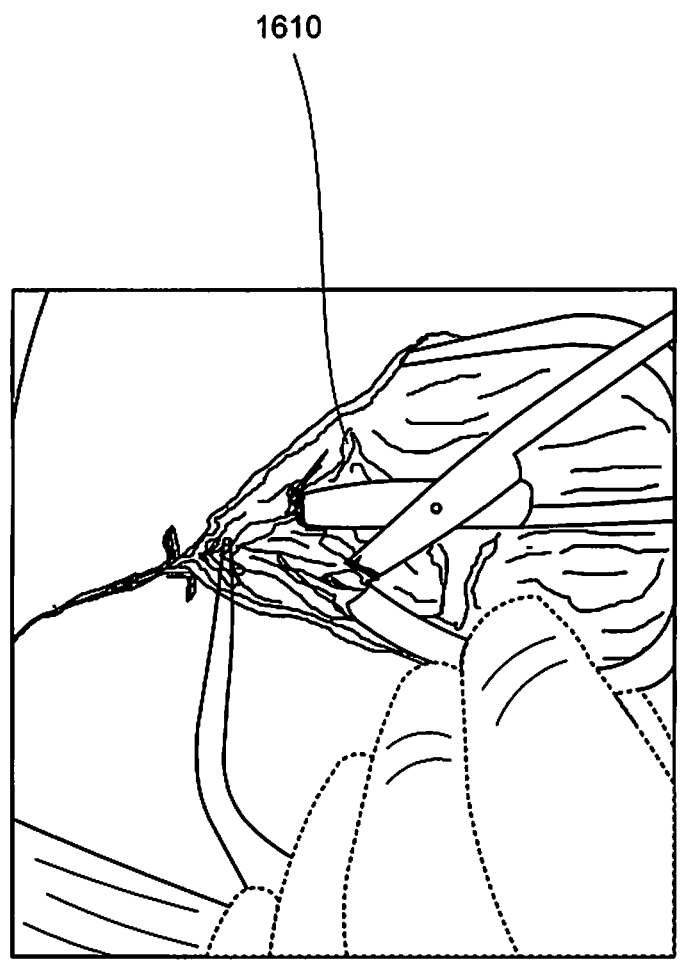

FIG. 18 illustrates a next step in the surgical technique. The next step may include splitting the muscle in the patient above the desired surgical destination. For example, in a lateral technique that will address a spinal disc, the external oblique muscles, internal oblique muscles and transverse abdominal muscles are split in line with the fibers of each level. In an example technique, it is contemplated that during this step to be cognizant of cutaneous nerves while moving between the muscle layers. One or more surgical instruments may be used during this step of the technique. For example, a combination of the Long Metzenbaum Scissors, forceps, bipolar forceps, and 8 inch suction may be used.

Figure 19:
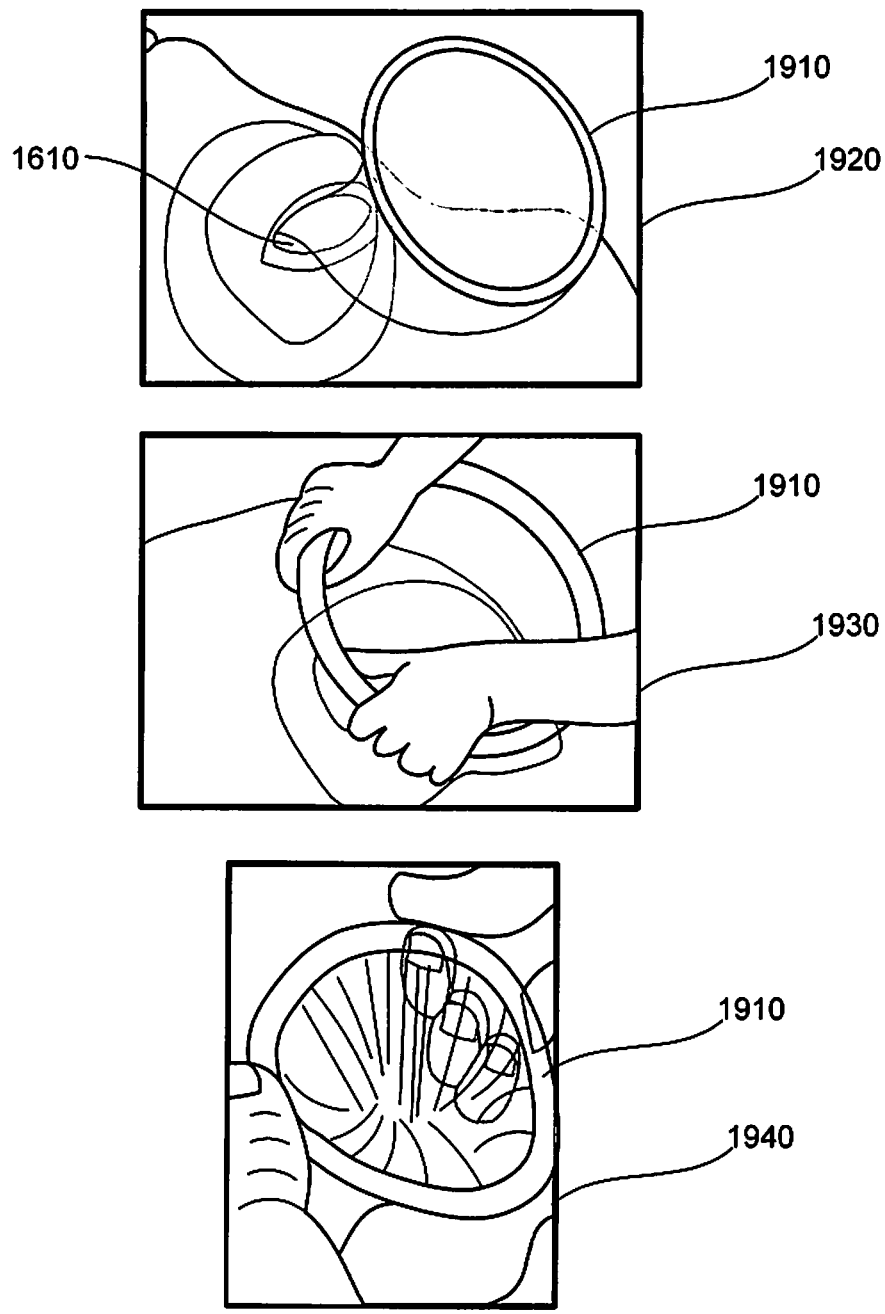

FIG. 19 illustrates a next step in the example surgical technique. The next step may include inserting a retractor into the incision 1610. For example, once the external oblique muscles, internal oblique muscles, and transverse abdominus muscles have been split, a flexible wound retractor 1910 may be inserted. The flexible wound retractor 1910 may be self-retaining and may provide a consistent surgical corridor to access the surgical site. For instance, the flexible wound retractor 1910 may provide a consistent surgical corridor to access the psoas.

The first part of the step is illustrated in image 1920. The image 1920 illustrates inserting the retractor 1910 by first squeezing a blue ring to collapse while inserting into the incision 1610. The blue ring should rest on top of the psoas muscle. The ring may be gently pulled to ensure proper fit in the incision 1610, with the white ring positioned on top of the skin. The next portion of the step is illustrated in the image 1930. In the image of 1930, the hands are positioned at 11 and 1 o'clock. The next portion of the step is illustrated in the image 1940. In this image, the white ring is rolled down outwards first with the left hand and followed by the right hand. This process is repeated 2 to 3 times until desired exposure is achieved.

FIGS. 20-23 illustrate the next step in the surgical technique. In this step illustrated by FIGS. 20-23, the medical device 10 described above with respect to FIGS. 1-8 is inserted into the incision. As discussed above, medical device 10 may be referred to as a peritoneal retractor that is inserted into the incision to help retract the peritoneum out of the surgical corridor. The use of the medical device 10 may begin by first attaching the table clamp over the drape and onto the bed rail attachment. Then, the articulating arm assembly may be inserted into the clamp and secured.

Figure 20:
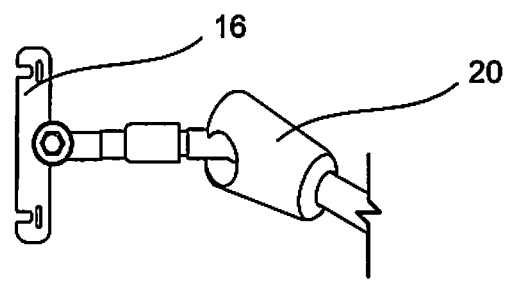
Figure 21:
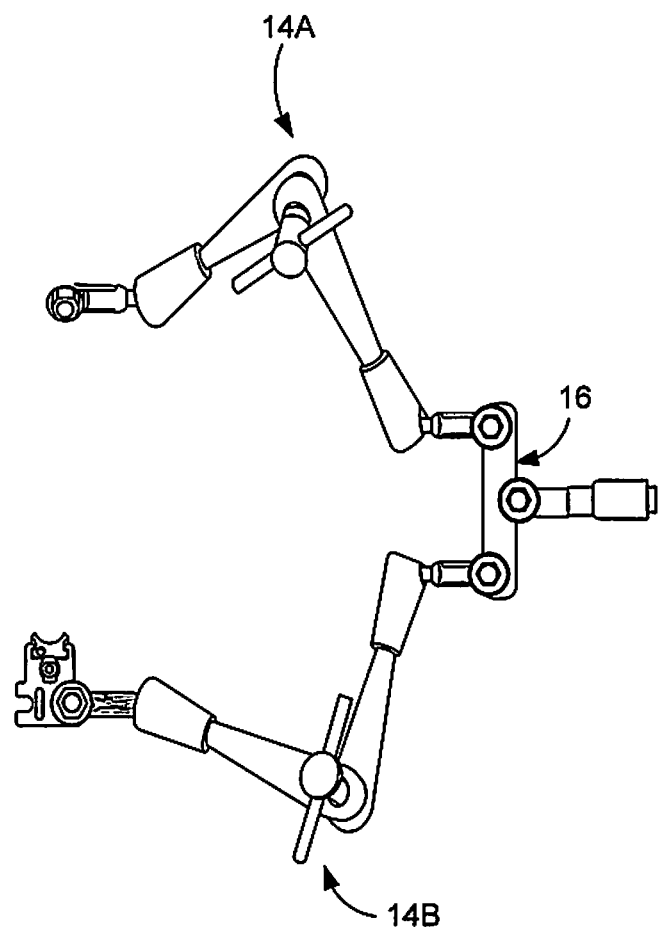
Figure 22:
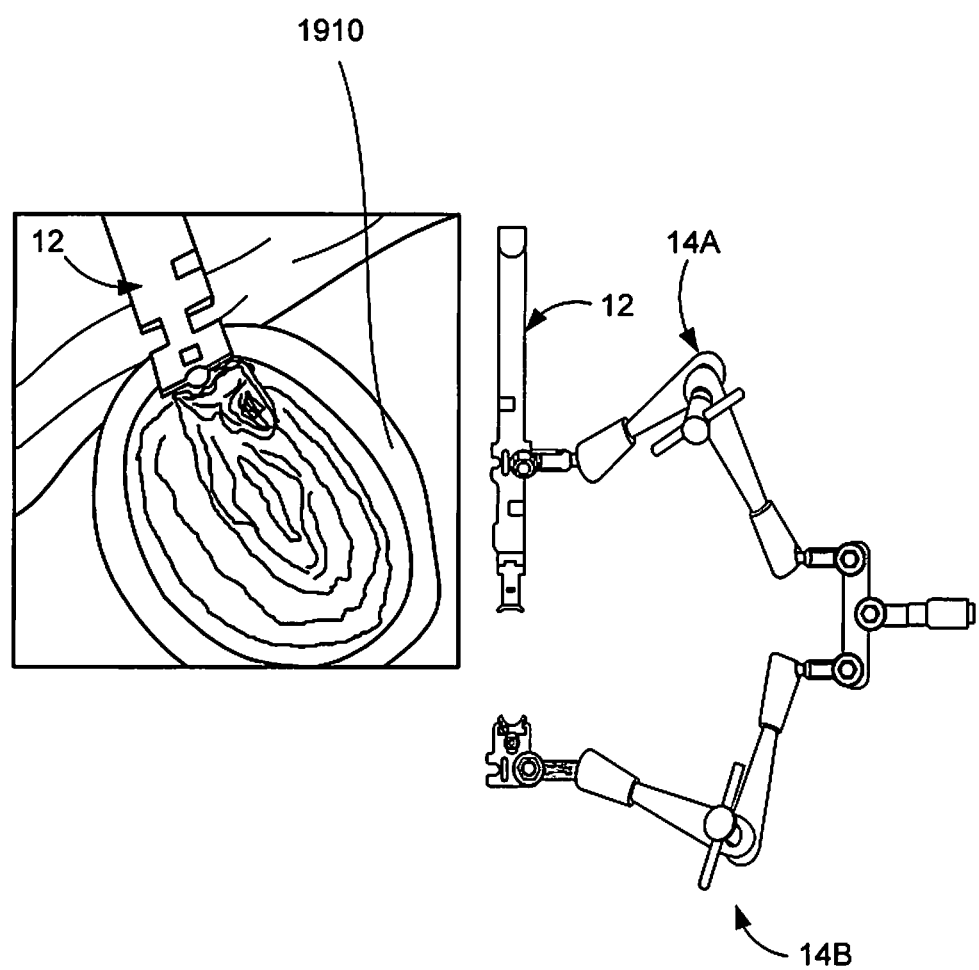

FIG. 20 illustrates attaching the mounting bracket 16 to the table arm 20. FIG. 21 illustrates attaching the arms 14A and 14B to the mounting bracket 16. Next, FIG. 22 illustrates the attachment of the retractor assembly blade 12 to the arm 14A and inserting the retractor assembly blade 12 through the flexible wound retractor 1910. Prior to insertion into the flexible wound retractor, an appropriate sized blade may be selected for attachment to the retractor assembly blade 12. The retractor assembly blade 12 is inserted through the flexible wound retractor 1910 to secure the peritoneum anteriorly. The retractor assembly blade 12 may be individually positioned as needed by unlocking the arm 14A such that it may move into any desired position and or plane and then locking the arm into the desired position. As discussed above, the arm 14A and its attached retractor assembly blade 12 may be individually positioned as needed separate from the arm 14B and any of blade attached to that arm.

Figure 23:
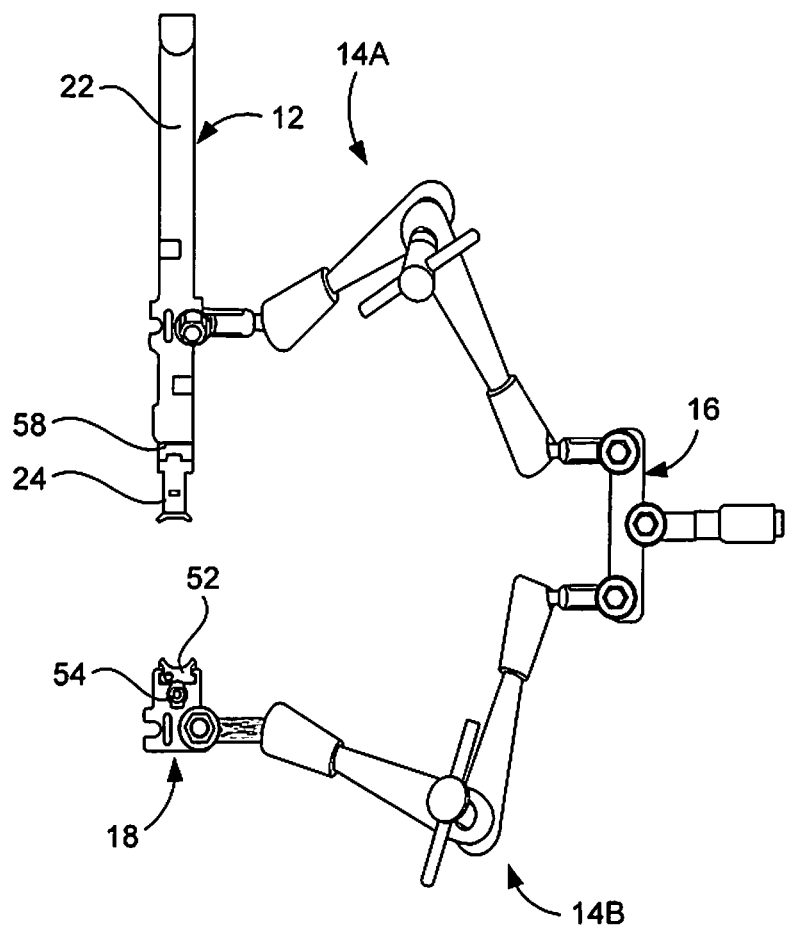

FIG. 23 illustrates that a blade may be attached to the arm 14B through the mounting bracket 18. For example, a MARS 3V posterior blade from Globus Medical Inc. may be attached to retract the posterior wall of the surgical corridor. In the illustrated example, the blade mounting bracket 18 is secured to the arm 14B. The desired posterior blade 52 can then be attached to the bracket 18 using a hook and latch driver and locked into position using the locking mechanism 54.

As described above with respect to the medical device 10, the blade 24 in the retractor assembly blade 12 may be positioned relative to the handle portion 22 of the retractor assembly blade using the hinge pin 58. The blade 24 and the blade 52 may be independently moved and/or adjusted as needed by loosening the respective arms 14A and 14B, repositioning the arms 14A and 14B to a desired position and re-locking the arms in the desired position.

Figure 24:
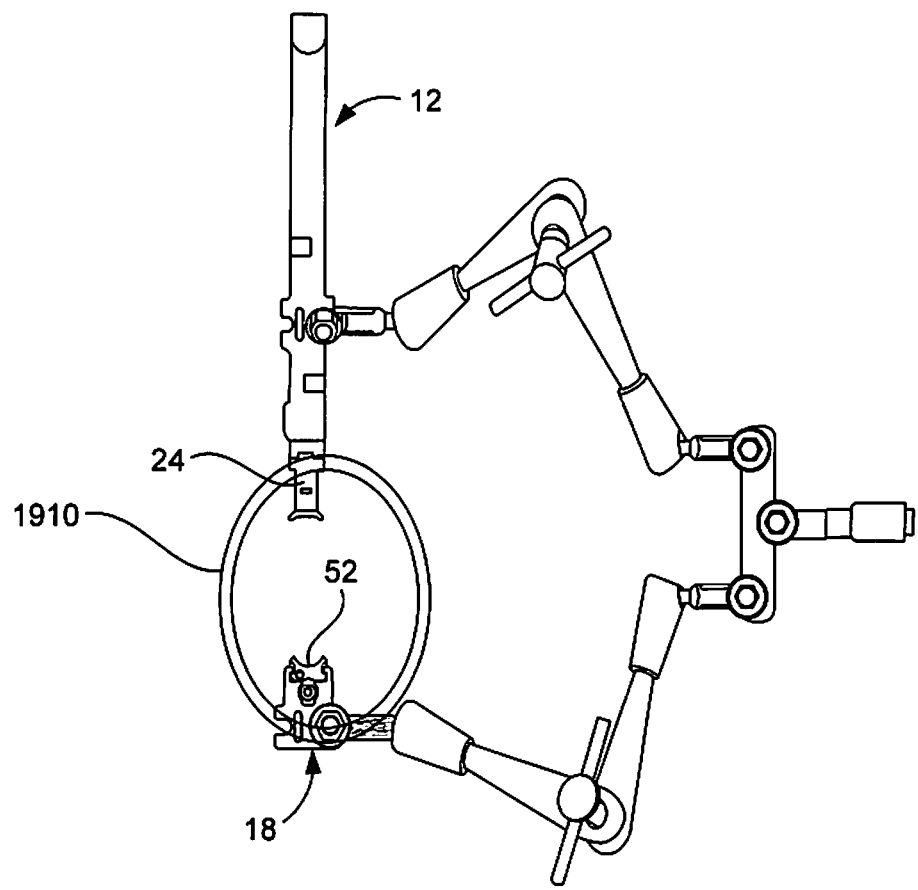
Figure 25:
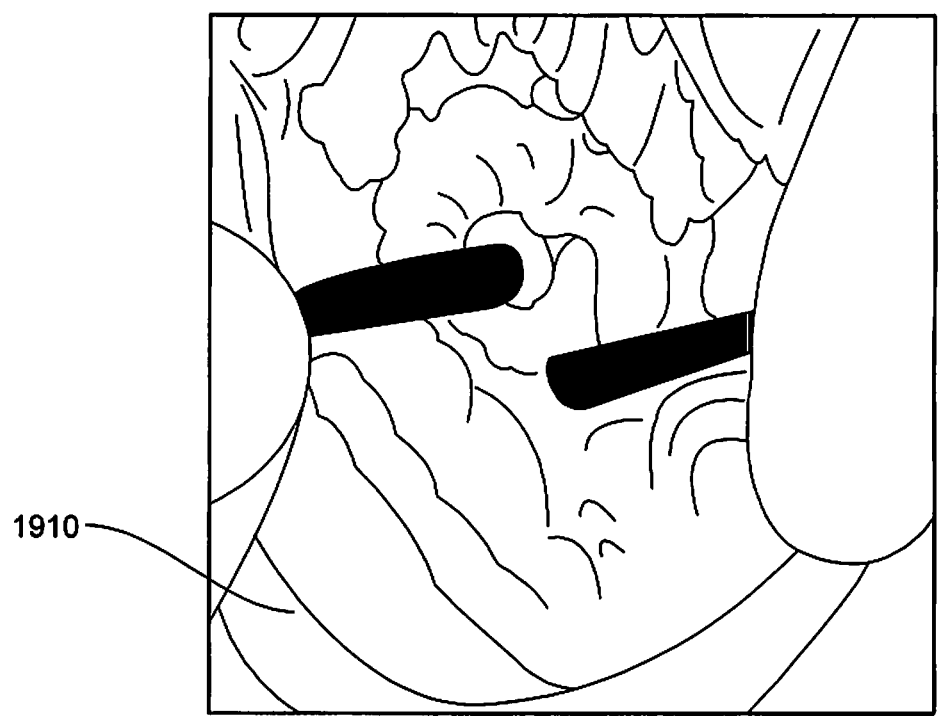

FIGS. 24 and 25 described the next step in the example surgical technique. The next step may be performed through the medical device 10. In this step, access is provided to the transpsoas. First, the genitofemoral nerve may be located and swept to the posterior aspect of the surgical corridor. The psoas fascia may be opened using a combination of endoscopic kitners and Metzenbaum scissors. Releasing the fascia releases tension on the muscle and the genitofemoral nerve, allowing a safer passage for sequential dilation.

Figure 26:

FIG. 26 illustrates a next step in the surgical technique. In the next step, sequential dilation may be performed. As part of the sequential dilation, the K-wire stop described above with respect to FIGS. 9-11 may be used. The K wire stop, which is optional, may be deployed concurrently with an initial dilator. The initial dilator may be placed with the K-wire extending through a lumen of the initial dilator and the K-wire stop may be used to limit how far the K-wire will extend from the lumen at the distal end of the dilator. The K-wire may be sized so that it will be abut the proximal end of the initial dilator preventing the K-wire from extending further through the lumen of the initial dilator. Once the K-wire and initial dilator reach the desired location, the stop can be loosened and removed allowing the K-wire to be pushed into the tissue to be addressed to serve as a locational guidepost. Then, sequential dilation may take place and the retractor described in the next figures may be placed over the largest dilator. For example, a first cannula may be used to locate the appropriate part of the disc for K-wire insertion and may be verified with fluoroscopy, as needed. The disc may feel like a small bump on the lateral aspect of the spine. The lumbar plexus branches should be posterior to the first cannula and not docked within a branch of the plexus. The K-wire may be inserted through the first cannula and into the disc and sequential dilation may be used using multiple cannulas such as second and third cannulas.

FIGS. 27-38 described the next step in the example surgical technique. In this example step, a retractor may be used and inserted to access the surgical site and provide assistance in direct visualization of the surgical site. In one example embodiment, a MARS 3V retractor from Globus Medical, Inc. may be used. The retractor, such as the one described in U.S. Pat. No. 8,353,826 (the '826 patent) may be used to retract the tissue. The '826 patent is hereby incorporated by reference in its entirety.

Figure 27:
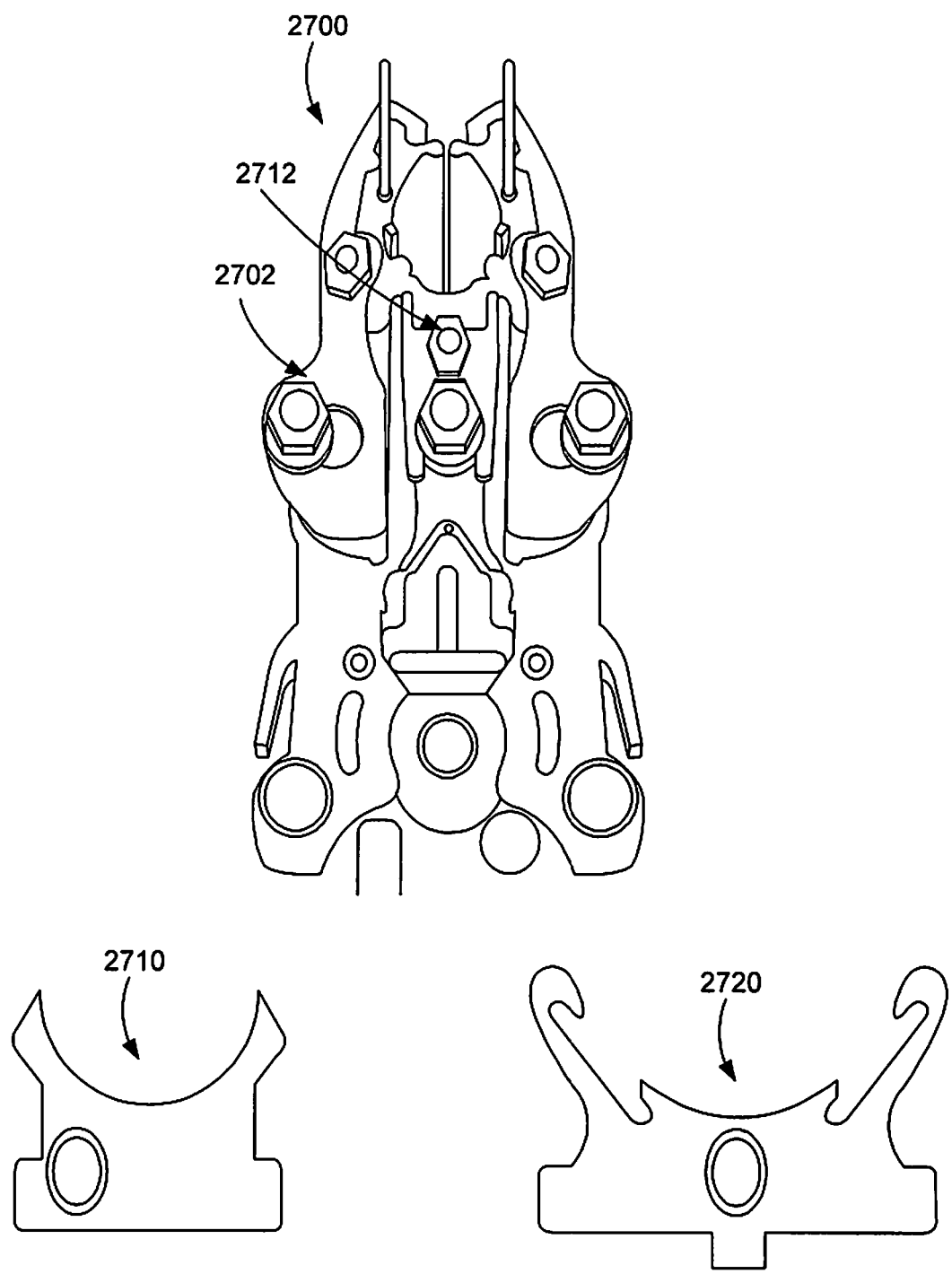

FIG. 27 illustrates the retractor 2700. The appropriate blades may be selected and inserted into each of the three blade mounts of the blade frame 2702. For example, a posterior blade 2710 may be inserted into the posterior blade mount 2712. For the other blades, a cephalad-caudal (CC) blade 2720 may be inserted into the other blade mounts.

Figure 28:
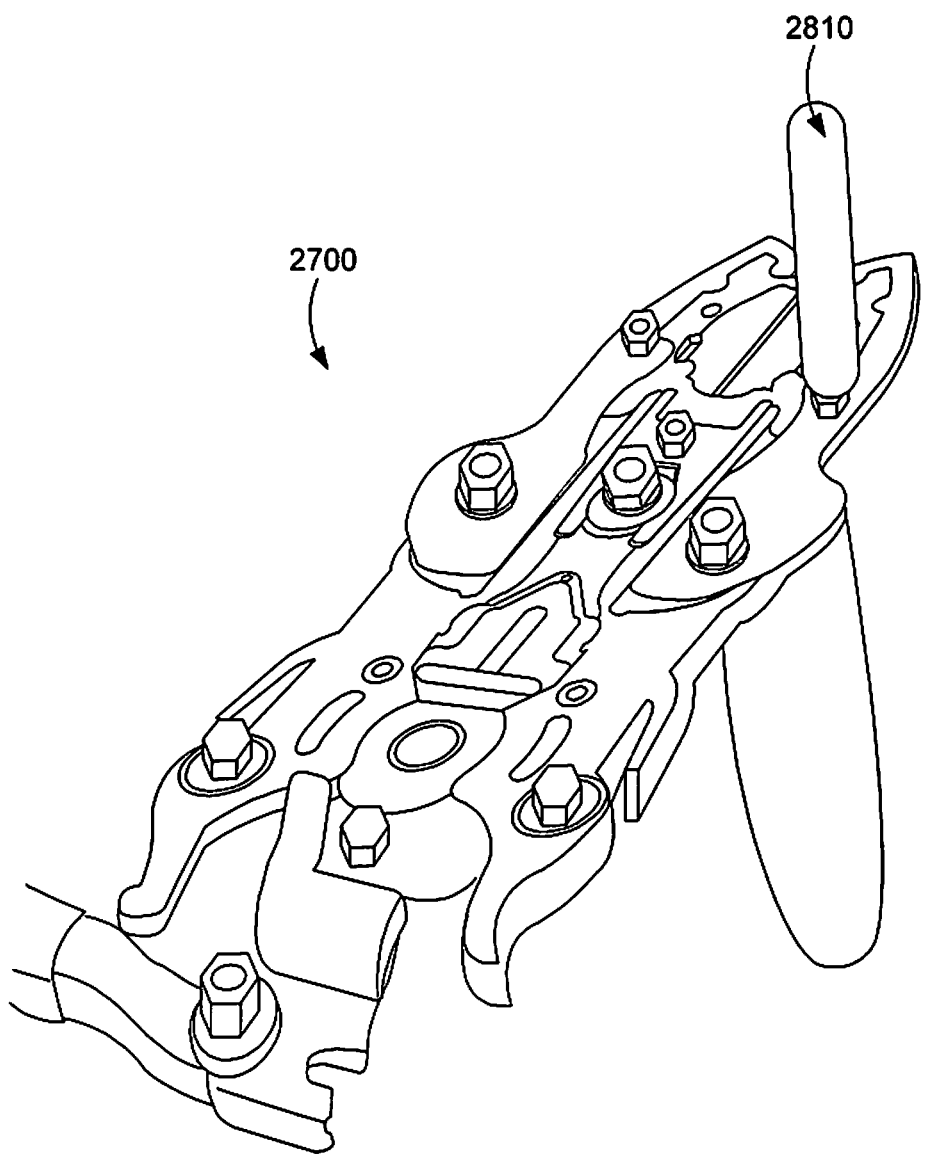

FIG. 28 illustrates ensuring that the blades are properly seated into the retractor 2700. For example, the blades should be properly seated into the retractor 2700 at each of the three positions. The blades may be secured using a hook and latch driver 2810. The driver 2810 may be positioned on the latch and rotated 90° clockwise to lock the blade in place. The blades can be changed intra-operatively when a different blade length is required. The blades include angled holes to accept the driver. The driver may be inserted and tightened down on the white sleeve to hold the blade securely. This provides a secure connection to remove the blade.

Figure 29:
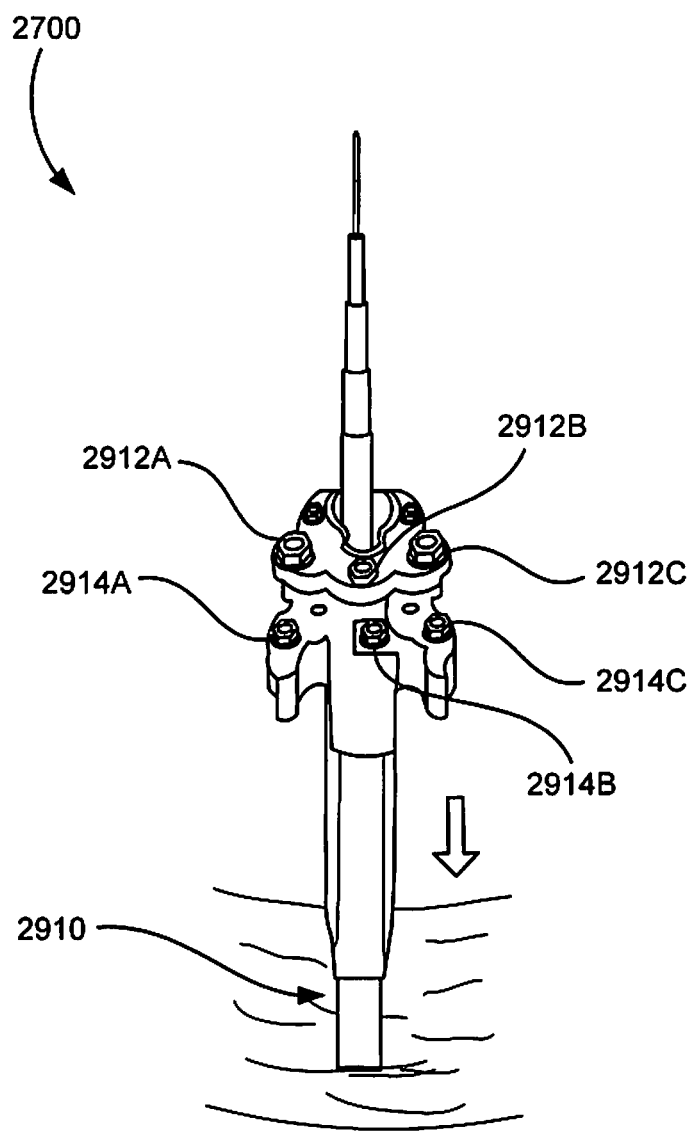

FIG. 29 illustrates the retractor positioning. Ensure that the retractor 2700 is in the fully closed position and the blades are securely attached to the frame. The access incision should allow the blades to retract and angulate. Slide the retractor over the third cannula 2910 and apply gentle downward pressure on the frame. Before removing the cannulas, angulate all three blades to one full turn of the silver knobs 2912A-2912C. Retract all three blades to two clicks using the gold knobs 2914A-2914C. The blade closest to the iliac crest should be retracted first. Angulating and retracting the blades in this manner will help prevent tissue creep as the cannulas are removed.

At this point, the peritoneal retractor, or medical device 10, may be detached from the articulating arm assembly use a 10 mm socket driver to remove the arm mounting bracket from the arm. Position the arm and attach to the MARS 3V retractor mounts. Once the retractor has been securely positioned and the arm tightened, remove the cannulas and verify the position of the retractor before removing the K-wire. AP fluoroscopy may be used to verify the correct positioning on the spine and to confirm that the retractor blades are parallel with the disc space.

Figure 30:
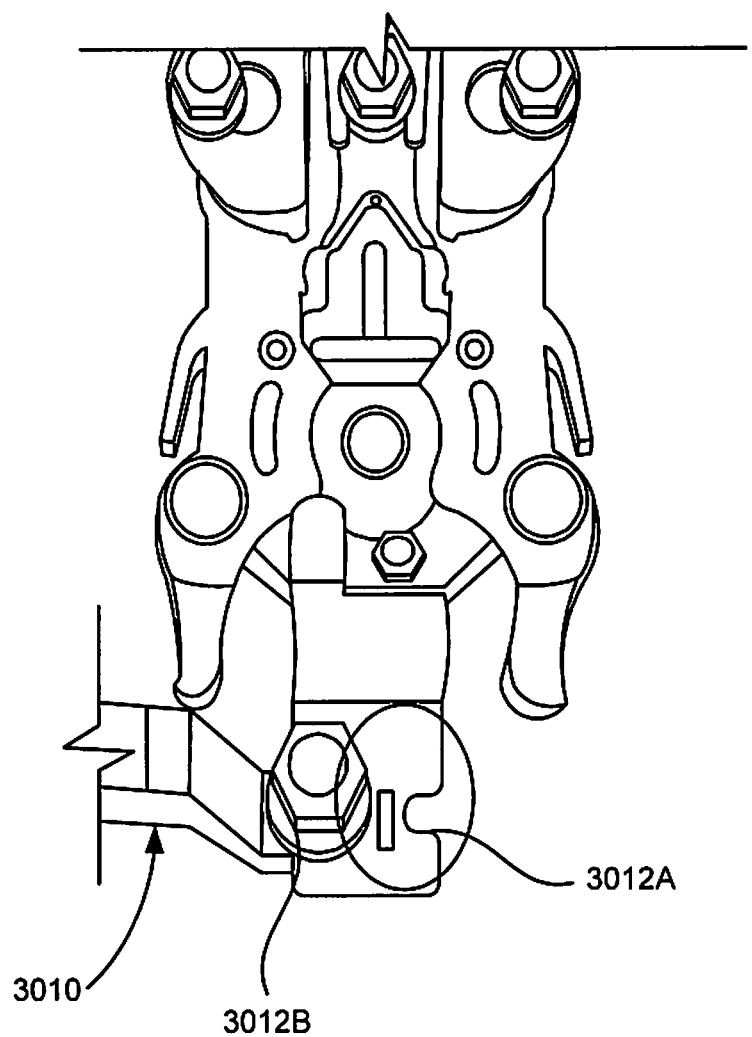

FIG. 30 illustrates the attachment of the medical device 2700 to the table arm 3010. The table clamp may be attached over the drape and onto the bed rail attachment. The articulating arm assembly may be inserted into the clamp and secured. The opposite end of the assembly arm is then attached to the retractor 2700. There are two options for attachment positions on the retractor as shown in FIG. 30 at 3012A and 3012B. Attaching the arm assembly to 3012 a maintains retract position relative to the posterior blade position and translates the cephalad and caudal blades interiorly when the retractor is opened. Attaching the arm assembly to attachment 3012B maintains the retractor position relative to the center of the frame and retracts all three blades when the retractor is opened.

Figure 31:
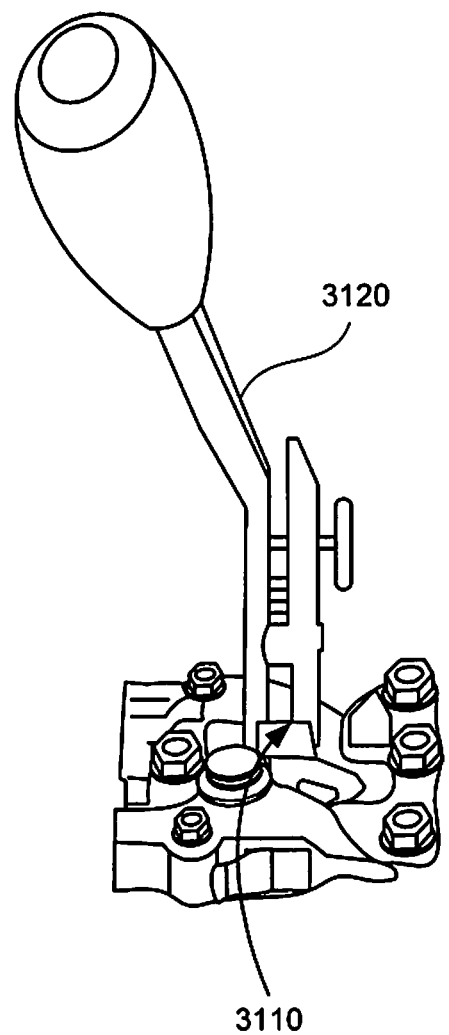

FIG. 31 illustrates the table arm attachment. The articulating arm assembly may be inserted into the desired attachment positioned and tightened the thumbscrew 3110 using a 10 mm socket driver 3120. The arm may be positioned and locked in place by tightening the handle on the arm assembly. Minimal torque may be required to tighten the thumbscrew with the driver 3120. Manipulation of the retractor can be achieved with the frame handle that fits over the arm attachment point.

Figure 32:
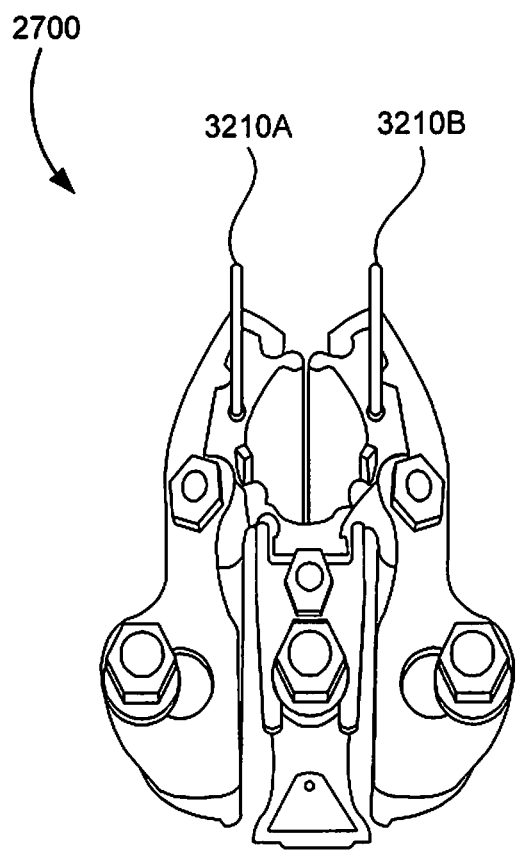

FIG. 32 illustrates the light cable insertion into the retractor 2700. One or more light cables 3210A and 3210B may be inserted into the blades. The light cables should be inserted through the blade to a depth providing optimal visibility. The fiber optic cord may attach to the light source used for headlamps or endoscopes. The adapters accommodate an ACMI, Olympus, Storz, or Wolf light source.

Figure 33:
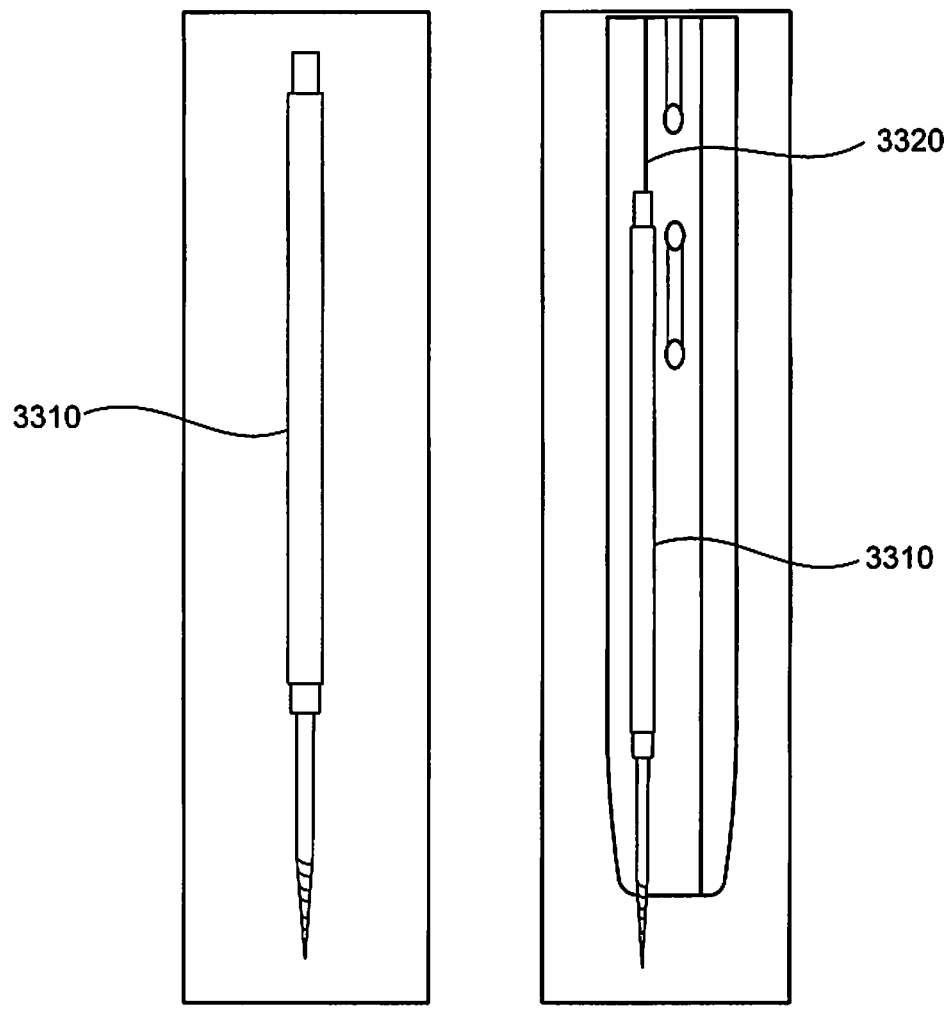
Figure 34:
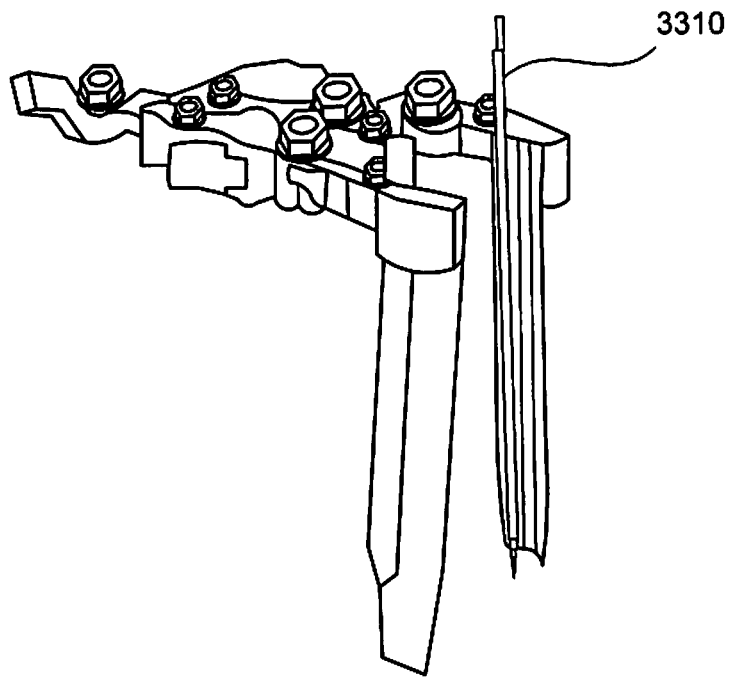
Figure 34:
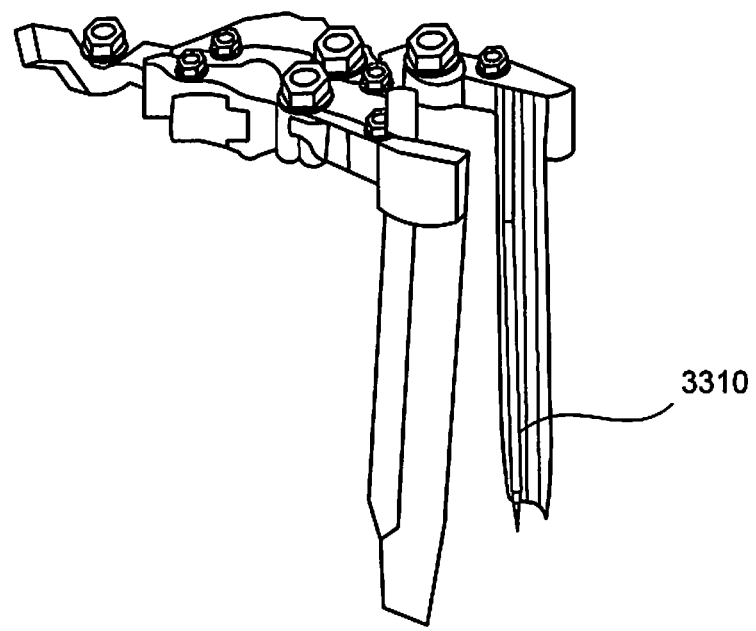

FIGS. 33 and 34 illustrate the cephalad-cauded blade anchoring. For additional retractor stability, docking pins such as docking pins 3310 may be inserted into the vertebral body through the blades to increase retractor stability when expanding the blades for greater exposure as shown in FIG. 34. Different size pins may be used and inserted into the docking pin sleeve 3320. The pin assembly can slide down the T-slot on either side of the blade. The docking pin tool includes a hex feature that mates with the head of the pin. The tool may be rotated clockwise to engage pin threads into the bone. To remove the pins, re-engaged the hex of the tool into the pin head and rotate counterclockwise to disengage from the bone.

Figure 35:
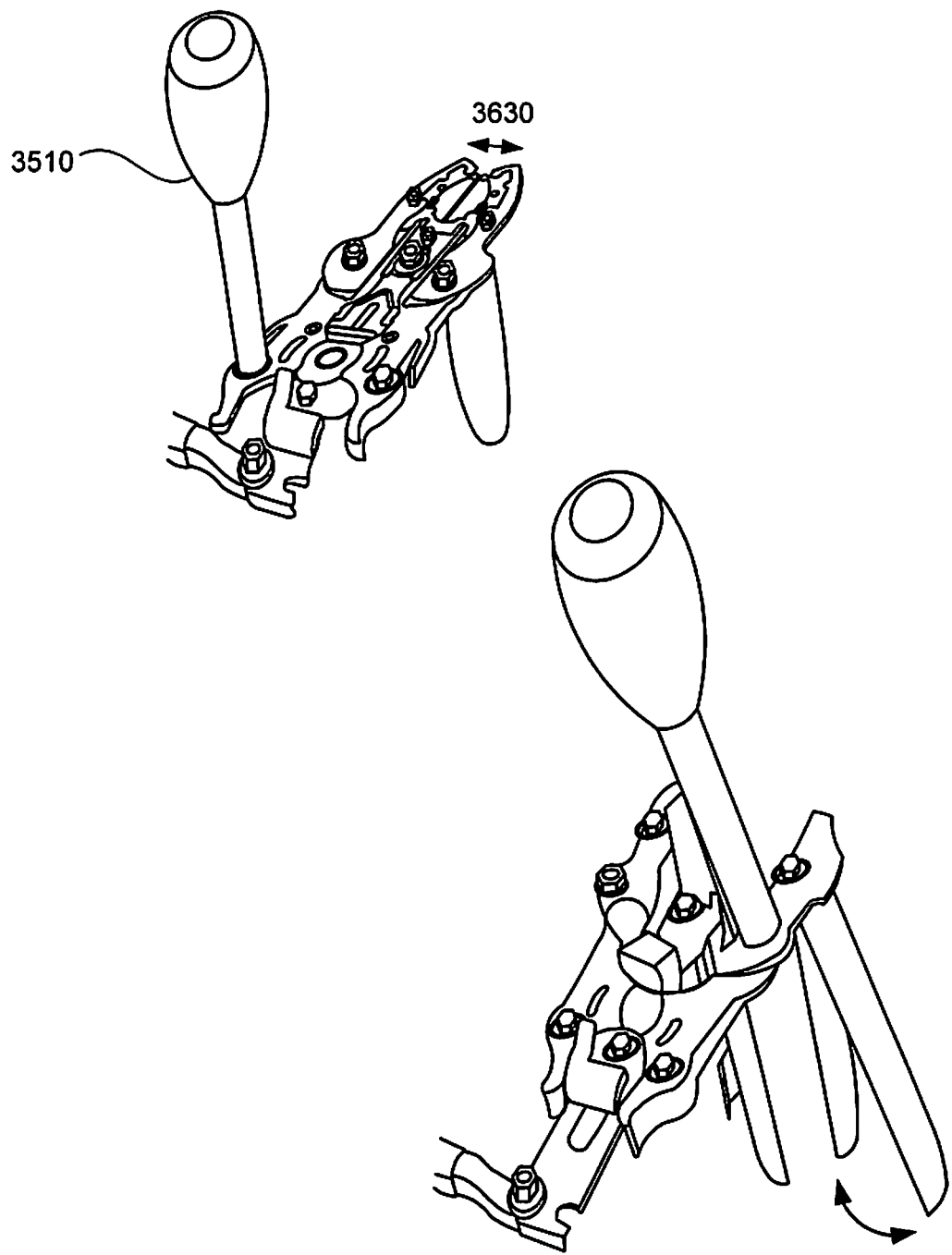

FIGS. 35-38 illustrate the blade expansion of the retractor 2700. Each blade may be independently expanded using the 10 mm socket driver 3510 to rotate the respective gold hex nut in the direction indicated by the arrow 3630. Each blade may be angled up to 20° using the driver. The driver 3510 may be placed onto the silver hex nut and rotate the instrument clockwise, allowing the blade to tilt to the desired position as illustrated in FIG. 35.

Figure 36:
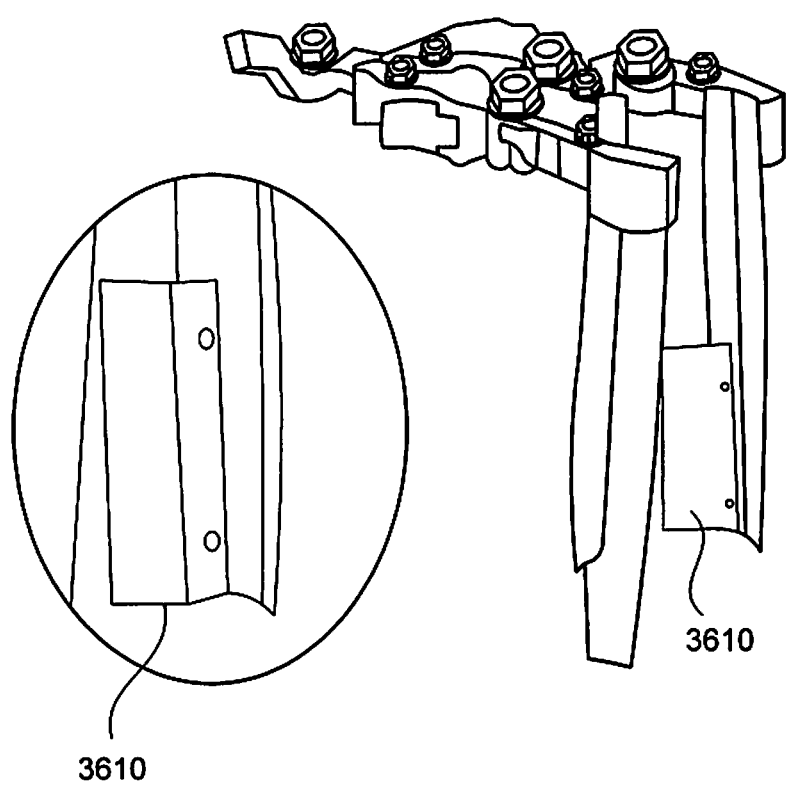

As illustrated in FIG. 36, a widening shim 3610 may be used to prevent soft tissue creep between blades. The shim 3610 may be used to slide down the T-slot on either side of the blades for an additional 22 mm of blade width. The shim provides additional blade width. In other example embodiments, the shim may provide other widths. A tool may be used to insert the shim down the T-slot on either side of the blades.

Figure 37:
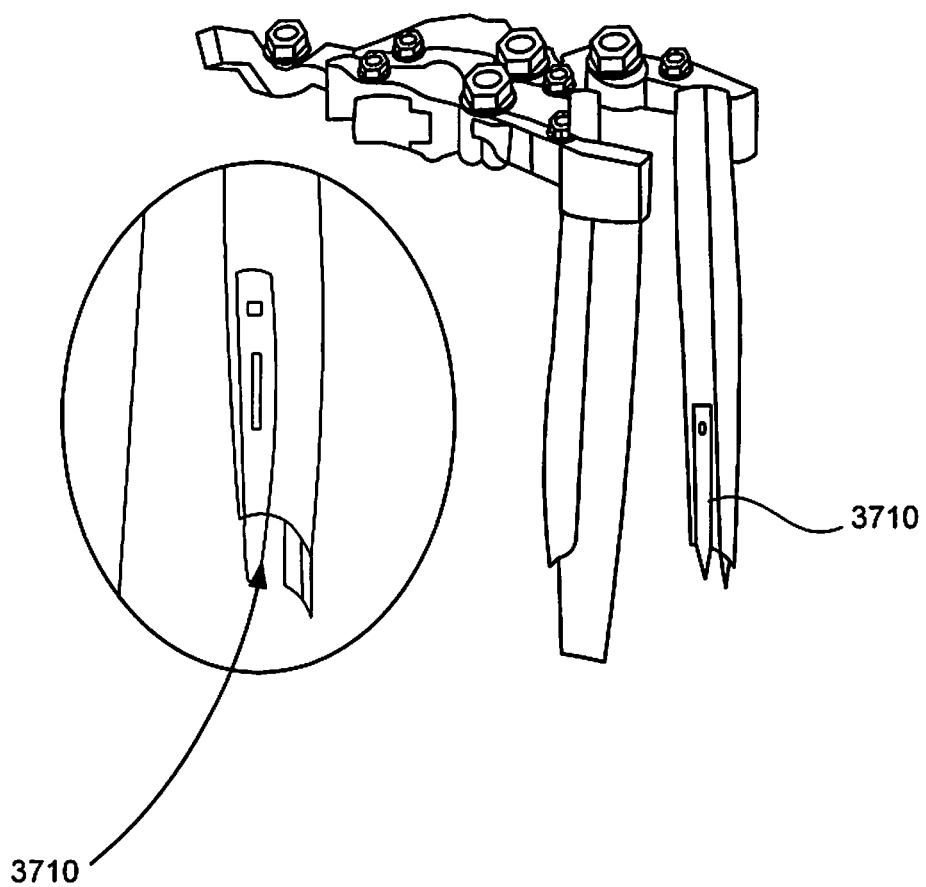

FIG. 37 illustrates the use of a lengthening shim 3710. The lengthening shim 3710 may be used to help prevent soft tissue creep between blades by increasing the length of the blade to maintain bone contact. While angulating the CC blades, lengthening shims can be used. A shim tool may be used to push the lengthening shim down the right T-slot of the blades.

Figure 38:
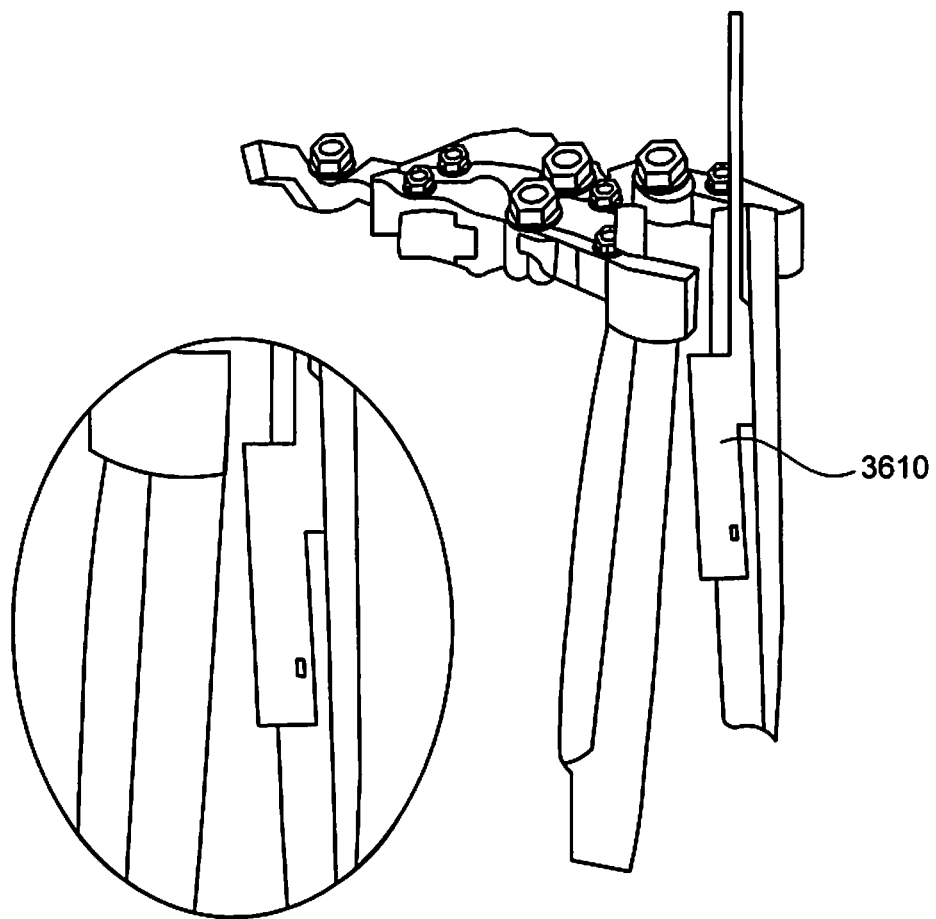

FIG. 38 illustrates the removal of the widening shim 3610 and the lengthening shim 3710. Both the widening and lengthening shims have angled holes to accept the hook on the shim tool. The hook may be inserted and pulled upwards to remove the shims.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments. It should be understood that they have been presented by way of example only, not limitation, and various changes in form and details may be made. Any portion of the apparatus and/or methods described herein may be combined in any combination, except mutually exclusive combinations. The embodiments described herein can include various combinations and/or sub-combinations of the functions, components and/or features of the different embodiments described.

What is claimed is:

1. A method for retracting tissue in a surgical procedure comprising:
    inserting a first blade of a retractor system into an incision in a body of a patient, wherein the retractor system includes a first articulating arm and a second articulating arm, the first articulating arm coupled to a retractor assembly, the retractor assembly having a handle portion extending from a distal end to a proximal end and directly coupled to the first blade, the first blade being connected to the proximal end of the handle portion, wherein the first articulating arm connects to the handle portion near the proximal end of the handle portion of the retractor assembly and the second articulating arm directly coupled to a bracket securing a second blade;
    retracting tissue using the first blade;
    inserting the second blade into the incision in the body of the patient; and
    retracting tissue using the second blade;
    wherein the handle portion of the retractor assembly blade is pivotable with respect to the first blade,
    wherein the handle portion and the first blade are coupled through a hinge mechanism,
    wherein the handle portion and the first blade can be rotated and locked in multiple positions,
    wherein the hinge mechanism allows the first blade to be moveable relative to the handle portion only about a single axis,
    wherein the handle portion is elongated from the distal end to the proximal end, and
    the distal end includes a curved portion configured to allow pulling of the retractor assembly blade,
    wherein the first articulating arm is directly coupled to the retractor assembly and the second articulating arm is directly coupled to the bracket and the bracket is directly coupled to the second blade,
    wherein each of the first and second articulating arms includes one or more component arms, and
    wherein each of the one or more component arms includes a corresponding knob portion configured to lock its corresponding component arm in a desired position
    wherein the bracket includes a first hook and second hook creating a first slot and a second slot for receiving the second blade,
    wherein the second blade is moveable within the first and second slot of the bracket.

2. The method of claim 1, further comprising independently positioning the first blade and the second blade using the first articulating arm and the second articulating arm, respectively.

3. The method of claim 1, wherein retracting tissue using the first blade comprises retracting a peritoneum anteriorly out of a surgical corridor.

4. The method of claim 3, wherein retracting tissue using the second blade comprises retracting a posterior wall of the surgical corridor.

5. The method of claim 1, further comprising positioning the first blade at an angle relative to the handle portion using the hinge mechanism.

6. The method of claim 1, further comprising:
    prior to inserting the first blade of the retractor system into the incision, inserting a flexible retractor into the incision to provide a surgical corridor to a surgical site.

7. The method of claim 1, further comprising:
    inserting a second retractor system into the incision, wherein the second retractor system comprises a frame having a plurality of blades and a plurality of movable arms with each of the plurality of blades coupled to the frame through one of the movable arms; and
    angulating each of the plurality of blades of the second retractor system.

8. The method of claim 7, further comprising retracting each of the blades of the second retractor system.

9. The method of claim 7, wherein inserting the second retractor system comprises inserting the second retractor system into the incision in a closed position.

10. The method of claim 7, wherein the plurality of blades comprises a single posterior blade and two cephalad-caudal blades.

11. The method of claim 7, further comprising inserting at least one light cable through at least one of the plurality of blades to illuminate a surgical site.

12. The method of claim 1, wherein the handle portion is connected to the first articulating arm at one or more connection points between the distal end and the proximal end of the handle portion, wherein the distal end of the handle portion extends beyond the one or more connection points.

13. The method of claim 1, wherein the first blade has a proximal end, a distal end, and a central blade portion connecting the proximal end and the distal end, wherein the distal end and the proximal end each have a width greater than the central blade portion.

14. A medical device, comprising:
    a first mounting bracket;
    a first articulating arm directly coupled to the first mounting bracket;
    a second articulating arm directly coupled to the first mounting bracket;
    a retractor assembly coupled to the first articulating arm, the retractor assembly having a handle portion extending from a distal end to a proximal end and directly coupled to a first blade, the first blade being connected to the proximal end of the handle portion, wherein the first articulating arm connects to the handle portion near the proximal end of the handle portion; and a second mounting bracket coupled to the second articulating arm, the second mounting bracket directly securing a second blade;

wherein the handle portion of the retractor assembly is pivotable with respect to the first blade, wherein the handle portion and the first blade are coupled through a hinge mechanism, wherein the handle portion and the first blade can be rotated and locked in multiple positions, wherein the hinge mechanism allows the first blade to be moveable relative to the handle portion only about a single axis, wherein the handle portion is elongated from the distal end to the proximal end, and the distal end includes a curved portion configured to allow pulling of the retractor assembly, wherein the first articulating arm is directly coupled to the retractor assembly and the second articulating arm is coupled to the second blade via the second mounting bracket, wherein each of the first and second articulating arms includes one or more component arms, and wherein each of the one or more component arms includes a corresponding knob portion configured to lock its corresponding component arm in a desired position wherein the bracket includes a first hook and second hook creating a first slot and a second slot for receiving the second blade, wherein the second blade is moveable within the first and second slot of the bracket.

15. The medical device of claim 14, wherein the first blade and the second blade are independently positioned using the first articulating arm and the second articulating arm, respectively.

16. The medical device of claim 14, wherein the handle portion of the retractor assembly blade includes an elongate member with a first mounting location on one side of the elongate member and a second mounting location on an opposite side of the elongate member, with either of the first mounting location or the second mounting location used to couple to the first articulating arm.

17. The medical device of claim 14, wherein the second mounting bracket includes a first mounting location on one side of the second mounting bracket and a second mounting location on an opposite side of the second mounting bracket, with either of the first mounting location or the second mounting location used to couple to the second articulating arm.

18. The medical device of claim 14, wherein the second mounting bracket includes a first mounting location on one side of the second mounting bracket and a second mounting location on an opposite side of the second mounting bracket to enable the second mounting bracket to couple to two articulating arms.

19. A method for retracting tissue in a surgical procedure comprising:

inserting a flexible retractor into an incision in a body of a patient to provide a surgical corridor to a surgical site;

inserting a first blade of a retractor system into the incision in the body of the patient through the flexible retractor, wherein the retractor system includes a first articulating arm and a second articulating arm, the first articulating arm directly coupled to a retractor assembly, the retractor assembly having a handle portion extending from a distal end to a proximal end and directly coupled to the first blade, the first blade being connected to the proximal end of the handle portion, wherein the first articulating arm connects to the handle portion near the proximal end of the handle portion and the second articulating arm directly coupled to a bracket securing a second blade;

retracting tissue using the first blade;

inserting the second blade into the incision in the body of the patient;

retracting tissue using the second blade;

performing sequential dilation using a plurality of dilators;

inserting a second retractor system into the incision over a largest of the dilators, wherein the second retractor system comprises a frame having a plurality of blades and a plurality of movable arms with each of the blades coupled to the frame through one of the movable arms; angulating each of the plurality of blades of the second retractor system; and retracting each of the plurality of blades of the second retractor system;

wherein the handle portion of the retractor assembly is pivotable with respect to the first blade, wherein the handle portion and the first blade are coupled through a hinge mechanism, wherein the handle portion and the first blade can be rotated and locked in multiple positions, wherein the hinge mechanism allows the first blade to be moveable relative to the handle portion only about a single axis, wherein the handle portion is elongated from the distal end to the proximal end, and the distal end includes a curved portion configured to allow pulling of the retractor assembly, wherein the first articulating arm is directly coupled to the retractor assembly and the second articulating arm is directly coupled to the bracket and the bracket is directly coupled to the second blade, wherein each of the first and second articulating arms includes one or more component arms, and wherein each of the one or more component arms includes a corresponding knob portion configured to lock its corresponding component arm in a desired position wherein the bracket includes a first hook and second hook creating a first slot and a second slot for receiving the second blade, wherein the second blade is moveable within the first and second slot of the bracket.

20. The method of claim 19, further comprising independently positioning the first blade and the second blade using the first articulating arm and the second articulating arm, respectively.

* * * * *